United States Patent
Takagi et al.

(10) Patent No.: US 10,149,656 B2
(45) Date of Patent: Dec. 11, 2018

(54) RADIOGRAPHIC IMAGE CAPTURING SYSTEM

(71) Applicant: Konica Minolta, Inc., Chiyoda-ku, Tokyo (JP)

(72) Inventors: Tatsuya Takagi, Mitaka (JP); Hiroaki Matsumoto, Yokohama (JP); Ryohei Ito, Hino (JP); Agus Suharno, Hachioji (JP); Tsuyoshi Kobayashi, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 214 days.

(21) Appl. No.: 15/093,093

(22) Filed: Apr. 7, 2016

(65) Prior Publication Data

US 2016/0302755 A1    Oct. 20, 2016

(30) Foreign Application Priority Data

Apr. 14, 2015   (JP) ................ 2015-082439

(51) Int. Cl.
*A61B 6/00*  (2006.01)
*G06T 5/00*  (2006.01)
*G06T 5/50*  (2006.01)

(52) U.S. Cl.
CPC .......... *A61B 6/505* (2013.01); *A61B 6/5241* (2013.01); *A61B 6/5252* (2013.01); *A61B 6/582* (2013.01); *A61B 6/588* (2013.01); *G06T 5/005* (2013.01); *G06T 5/50* (2013.01); *A61B 6/4283* (2013.01);
CPC ................ *A61B 6/585* (2013.01); *G06T 2207/20224* (2013.01)

(58) Field of Classification Search
CPC ... A61B 6/5258; A61B 6/5235; A61B 6/4233; A61B 6/4405; A61B 6/56; A61B 6/563; A61B 6/4266; A61B 6/5205; A61B 6/486; A61B 6/505; A61B 6/5241; A61B 6/5252; A61B 6/582; A61B 6/588; A61B 6/4283; A61B 6/585; G01T 1/20; G06T 5/50; G06T 2207/20224
See application file for complete search history.

(56) References Cited

U.S. PATENT DOCUMENTS

| | | | | |
|---|---|---|---|---|
| 2015/0245807 | A1* | 9/2015 | Tajima | A61B 6/563 378/98 |
| 2016/0135764 | A1* | 5/2016 | Wojcik | A61B 6/4233 378/62 |
| 2017/0372454 | A1* | 12/2017 | Takagi | A61B 6/4266 |

FOREIGN PATENT DOCUMENTS

JP    201245159 A    3/2012

* cited by examiner

*Primary Examiner* — Courtney Thomas
(74) *Attorney, Agent, or Firm* — Cantor Colburn LLP

(57) ABSTRACT

A radiographic image capturing system includes the following. A capturing stand includes a holder to hold radiographic image capturing devices. A radiation irradiator is able to irradiate the radiographic image capturing devices at once. An image processor generates images based on image data acquired by the radiographic image capturing devices. The image processor removes a structural component derived from the front radiographic image capturing device, on the basis of a calibration image and the generated image. The calibration image is preliminarily generated based on the image data acquired by the rear radiographic image capturing device with no subject disposed. The generated image is generated based on the image data acquired by the rear radiographic image capturing device during actual image capturing. The image processor removes a streaky component residing in the generated image.

13 Claims, 21 Drawing Sheets plong* p*1 p*2 p*3

RADIOGRAPHIC IMAGE CAPTURING SYSTEM

CROSS REFERENCE TO RELATED APPLICATIONS

The present invention claims priority under 35 U.S.C. § 119 to Japanese Application No. 2015-082439, filed Apr. 14, 2015, the entire content of which is incorporated herein by reference.

BACKGROUND OF THE INVENTION

Field of the Invention

The present invention relates to a radiographic image capturing system, specifically, a radiographic image capturing system including a capturing stand for capturing a long image by one-shot exposure.

Description of Related Art

An example of the recently developed capturing stands for supporting radiographic image capturing devices (flat panel detectors) used for capturing radiographic images of relatively large areas of a patient, such as a full spine or a full leg, (i.e., a long image) is, for example, with reference to FIG. 20A, a capturing stand 100 including a holder 101 carrying multiple radiographic image capturing devices P1 to P3 aligned along the body axis A of a patient H (in the vertical direction in FIG. 20A) (for example, refer to Japanese Patent Application Laid-Open No. 2012-045159). The number of radiographic image capturing devices P to be loaded in the holder 101 is not limited to three.

Capturing of a long image using such a capturing stand can be carried out by positioning the patient H and the holder 101 (i.e., the radiographic image capturing devices P1 to P3) and irradiating the multiple radiographic image capturing devices P1 to P3 once via the subject (i.e., patient H) with radiation from the radiation irradiator 102 (i.e., one-shot exposure).

Although not illustrated, traditional capturing of a long image is carried out by irradiating a single radiographic image capturing device P loaded in a holder with radiation multiple times from the radiation irradiator 102 while moving the radiographic image capturing devices P1 to P3 in the vertical direction. Unfortunately, the patient could move during movement of the radiographic image capturing device P together with the holder. Capturing a long image by one-shot exposure is advantageous in that such problem due to body movement does not occur.

As illustrated in FIG. 20A, capturing of a long image through a single exposure of the multiple radiographic image capturing devices loaded in the holder to radiation with a subject disposed in front of the radiographic image capturing devices is referred to as "capturing a long image by one-shot exposure." In the layout of the multiple radiographic image capturing devices in the holder, the bottom radiographic image capturing device P is disposed closer to the radiation irradiator 102 compared to the top radiographic image capturing device P in the holder 101, as illustrated in FIG. 20A, or the multiple radiographic image capturing devices P are staggered in the holder 101 so as to be alternately adjacent to or remote from the radiation irradiator 102, as illustrated in FIG. 20B.

Besides the vertical capturing stand 100 that captures a long image by one-shot exposure of the patient H in an upright position, as illustrated in FIGS. 20A and 20B, a horizontal capturing stand, such as that illustrated in FIG. 21, may also be used to capture a long image by one-shot exposure with radiation emitted once from above a recumbent patient H on a top panel 103 disposed above a holder 101 carrying horizontally aligned radiographic image capturing devices P1 to P3.

With reference to FIGS. 20A, 20B, and 21, edges of the radiographic image capturing devices P1 to P3 loaded in the holder 101 of the capturing stand 100 for capturing a long image by one-shot exposure overlap in view from the radiation irradiator 102. Thus, the radiographic image capturing device P in front from the radiation irradiator 102 is projected on the image acquired by the radiographic image capturing device P in the back from the radiation irradiator 102.

Among the radiographic image capturing devices loaded in a holder in a capturing stand according to the present invention, the radiographic image capturing device close to the radiation irradiator is referred to as a front radiographic image capturing device, and the radiographic image capturing device remote from the radiation irradiator is referred to as a rear radiographic image capturing device, in the case of not only the holder being installed in the vertical capturing stand 100 illustrated in FIGS. 20A and 20B, but also the horizontal capturing stand 100 illustrated in FIG. 21. Thus, the front radiographic image capturing device P in the capturing stand 100 illustrated in FIG. 21 is the top radiographic image capturing device P close to the radiation irradiator 102, and the rear radiographic image capturing device P is the bottom radiographic image capturing device P remote from the radiation irradiator 102.

With reference to FIG. 22A, an image p1 acquired by the rear radiographic image capturing device P1 (see FIG. 20A) contains transverse streaky components CL caused by linear structures, such as the edges of the casing and/or inner structure of the front radiographic image capturing device P2, and structural components CS caused by the structures in the casing of the front radiographic image capturing device P.

With reference to FIG. 22B, an image p2 acquired by the rear radiographic image capturing device P2 contains streaky components CL caused by linear structures, such as the edges of the casing and/or inner structure of the front radiographic image capturing device P3, and structural components CS caused by the structures in the casing of the front radiographic image capturing device P3.

The streaky components CL do not necessarily have a width of one pixel and could have a width of several pixels to several tens of pixels. The streaky components CL and the structural components CS in the image p1 illustrated in FIGS. 22A and 22B are depicted to contain pixels having pixel values of 0 for simplicity. Actually, the pixels of the streaky components CL and the structural components CS do not have pixel values of 0 but pixel values smaller than the original values.

As described above, the image p1 acquired by the rear radiographic image capturing device P containing the streaky components CL and the structural components CS cannot be precisely aligned and combined with the image p2 acquired by the front radiographic image capturing device P. Thus, the images cannot be combined to generate a long image.

BRIEF DESCRIPTION OF THE INVENTION

An object of the present invention, which has been conceived to solve the problem described above, is to provide a radiographic image capturing system that can acquire images by one-shot exposure that can be precisely corrected and combined to generate a long image.

According to an aspect of the present invention, there is provided a radiographic image capturing system including: a capturing stand which includes a holder which is able to hold a plurality of radiographic image capturing devices; a radiation irradiator which is able to irradiate the radiographic image capturing devices loaded in the holder at once with radiation; and an image processor which generates a plurality of images based on image data acquired by the radiographic image capturing devices, wherein, an edge of a front radiographic image capturing device overlaps in an anteroposterior direction with an edge of a rear radiographic image capturing device in the holder in view from the radiation irradiator, the front radiographic image capturing device being a radiographic image capturing device close to the radiation irradiator among the radiographic image capturing devices loaded in the holder, the rear radiographic image capturing device being a radiographic image capturing device remote from the radiation irradiator among the radiographic image capturing devices loaded in the holder, the image processor removes a structural component derived from the front radiographic image capturing device projected on a generated image, on the basis of a calibration image and the generated image, the calibration image being preliminarily generated based on the image data acquired by the rear radiographic image capturing device irradiated with radiation with no subject disposed in front of the radiographic image capturing devices loaded in the holder of the capturing stand, the generated image being generated based on the image data acquired by the rear radiographic image capturing device during actual image capturing of a subject, and the image processor removes a streaky component residing in the generated image on the basis of the generated image, to correct the image.

According to another aspect of the present invention, there is provided a radiographic image capturing system including: a capturing stand which includes a holder which is able to hold a plurality of radiographic image capturing devices; a radiation irradiator which is able to irradiate the radiographic image capturing devices loaded in the holder at once with radiation; and an image processor which generates a plurality of images based on image data acquired by the radiographic image capturing devices, wherein, an edge of a front radiographic image capturing device overlaps in an anteroposterior direction with an edge of a rear radiographic image capturing device in the holder in view from the radiation irradiator, the front radiographic image capturing device being a radiographic image capturing device close to the radiation irradiator among the radiographic image capturing devices loaded in the holder, the rear radiographic image capturing device being a radiographic image capturing device remote from the radiation irradiator among the radiographic image capturing devices loaded in the holder, the image processor removes a streaky component residing in the generated image based on the generated image, to correct the image, and the image processor subtracts a background component from a component acquired through horizontal smoothing of a region assigned in the image containing the streaky component during removal of the streaky component, to extract the streaky component, and adds the extracted streaky component to a pixel value of each pixel in the image, to remove the streaky component from the image.

According to the radiographic image capturing system of the present invention, it is possible to acquire images by one-shot exposure that can be precisely corrected and combined to generate a long image.

BRIEF DESCRIPTION OF THE DRAWINGS

The present invention will become more fully understood from the detailed description given hereinbelow and the appended drawings, and thus are not intended to define the limits of the present invention, and wherein.

DETAILED DESCRIPTION OF PREFERRED EMBODIMENTS

Figure 1:
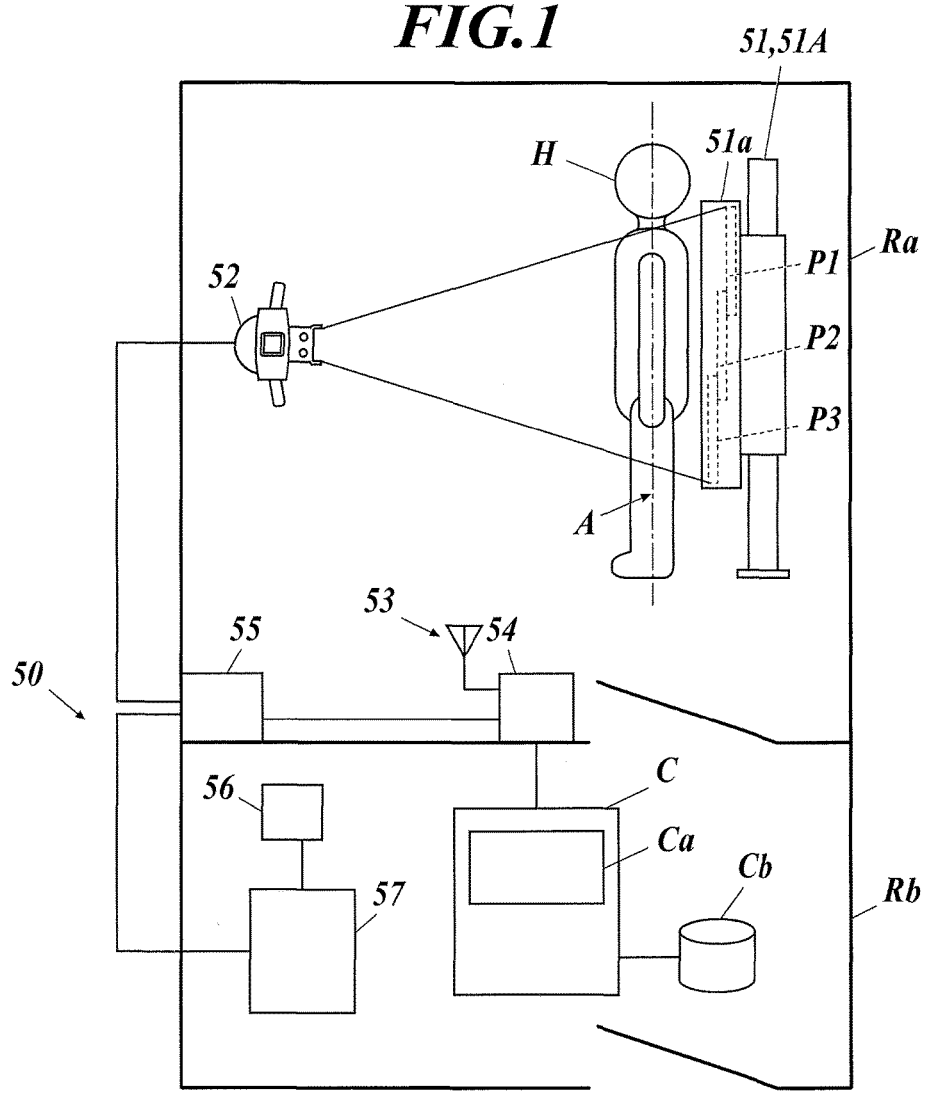
FIG. 1 illustrates the configuration of a radiographic image capturing system according to an embodiment.

A radiographic image capturing system according to an embodiment of the present invention will now be described with reference to the accompanying drawings. FIG. 1 illustrates the configuration of a radiographic image capturing system according to this embodiment.

FIG. 1 illustrates a capturing room Ra containing only a capturing stand 51A for capturing a long image by one-shot exposure. The capturing room Ra may also contain other capturing stands, such as a vertical capturing stand 51B and a horizontal capturing stand 51C for simple radiography (see FIG. 2). That is, when there is only one capturing room Ra, the capturing stand 51A for capturing a long image by one-shot exposure should be installed in the capturing room Ra and any other additional modalities may be optionally installed in the capturing room Ra.

The basic configuration of a radiographic image capturing system 50 according to this embodiment is illustrated in FIG. 1. One capturing room Ra is connected to one console C. Alternatively, two or more capturing rooms Ra (Ra1 to Ra3) may be connected to one or more consoles C (C1 and C2) via a network N, as illustrated in FIG. 2.

Figure 2:
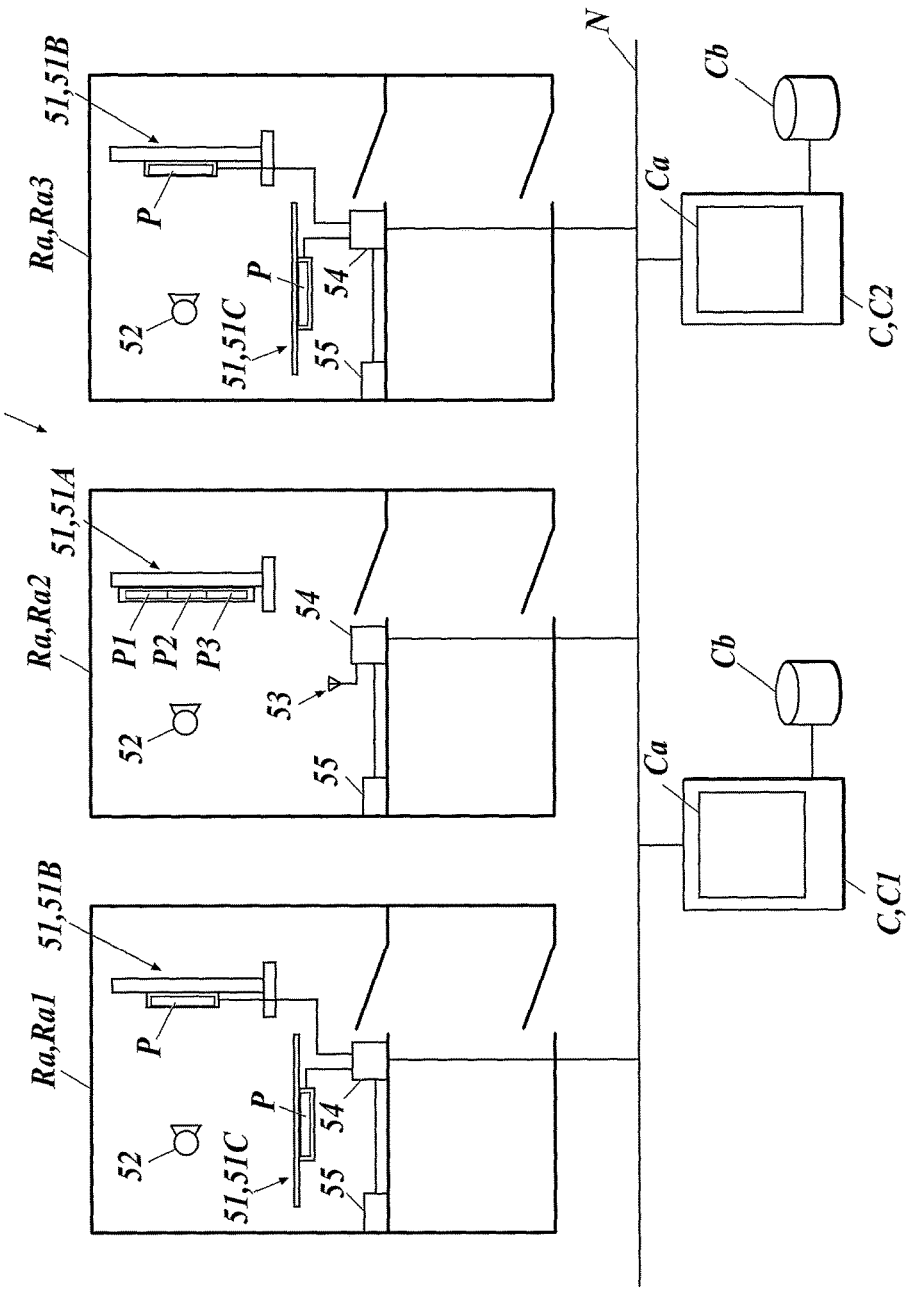
FIG. 2 illustrates an example configuration of a radiographic image capturing system including multiple capturing rooms linked to at least one console.

In multiple capturing rooms Ra as illustrated in FIG. 2, at least one of these capturing rooms Ra should be provided with a capturing stand 51A for capturing a long image by one-shot exposure, and any other additional modality may be optionally installed in the capturing room Ra containing the capturing stand 51A and the other capturing rooms Ra. Alternatively, a capturing stand 51A for capturing long image by one-shot exposure may be installed in all of the capturing rooms Ra.

Figure 21:
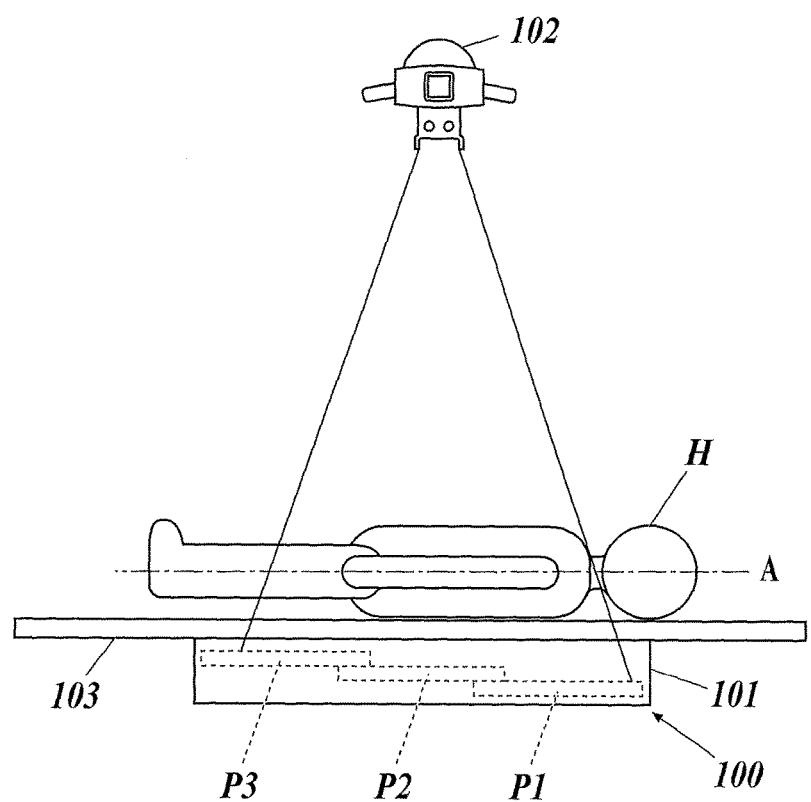
FIG. 21 illustrates an example configuration of a horizontal capturing stand for capturing a long image by one-shot exposure.

Hereinafter, the capturing stand 51A for capturing a long image by one-shot exposure may also be simply referred to as "capturing stand 51A". FIGS. 1 and 2 illustrate upright image capturing of a patient (not shown in FIG. 2) standing in front of the capturing stand 51A for capturing a long image by one-shot exposure. Alternatively, the capturing stand 51A for capturing a long image by one-shot exposure according to the present invention may be applied to recumbent image capturing of a patient laying or sitting on a top panel above a holder carrying multiple radiographic image capturing devices, as illustrated in FIG. 21.

[Configuration of Radiographic Image Capturing System]

With reference to FIG. 1, the capturing room Ra (or at least one of the multiple capturing rooms Ra (see FIG. 2)) according to this embodiment contains a capturing stand 51A for capturing a long image in a single exposure, which can hold multiple radiographic image capturing devices P1 to P3 for capturing a long image. The capturing stand 51A includes a holder 51a that can carry radiographic image capturing devices P1 to P3 aligned along the body axis A of a subject or patient H.

Hereafter, the radiographic image capturing devices P1 to P3 will be collectively referred to as radiographic image capturing devices P, unless they should be differentiated. With reference to FIGS. 1 and 2, loading of three radiographic image capturing devices P in the holder 51a of the capturing stand 51A will now be described. Alternative to three radiographic image capturing devices P, two, four, or more radiographic image capturing devices P may be loaded in the capturing stand 51A in the present invention.

Figure 20A:
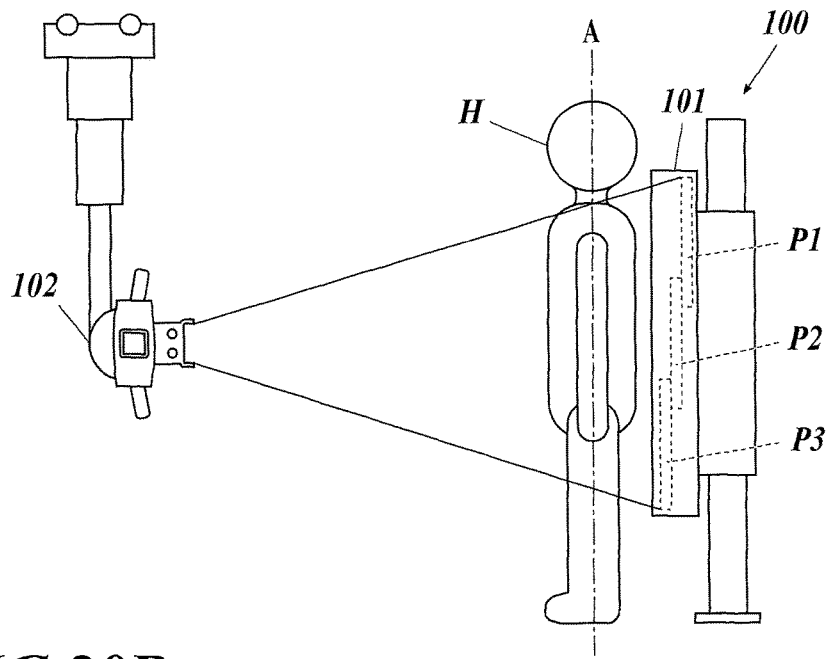
FIG. 20A illustrates an example configuration of a capturing stand for capturing a long image by one-shot exposure.
Figure 20B:
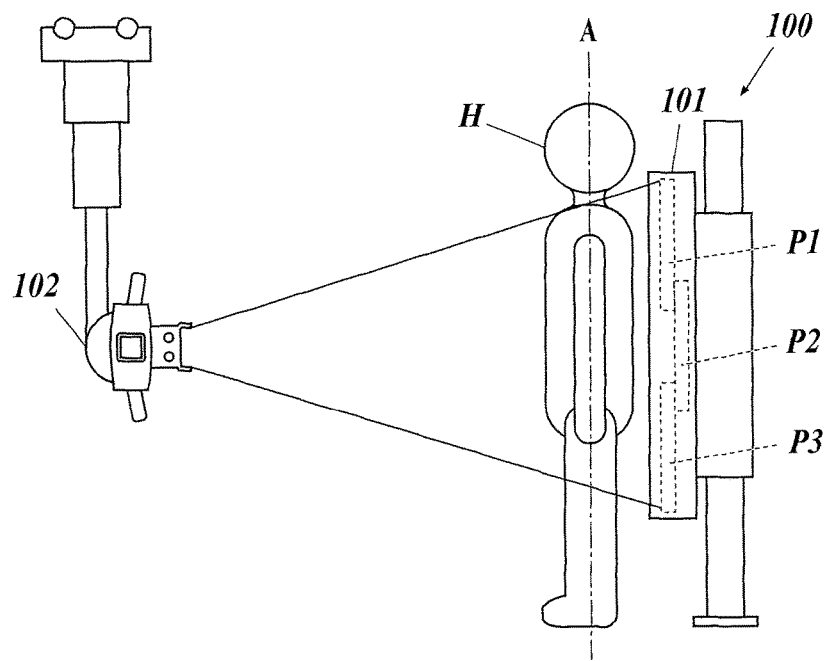
FIG. 20B illustrates another example configuration of a capturing stand for capturing a long image by one-shot exposure.

With reference to FIG. 1, multiple radiographic image capturing devices P are loaded in the holder 51a such that the lower radiographic image capturing devices P (P2 and P3) are disposed closer to the radiation irradiator 52 than the higher radiographic image capturing devices P (P1 and P2). Alternatively, multiple radiographic image capturing devices P1 to P3 may be staggered in the holder so as to be alternately close to or remote from a radiation irradiator, as illustrated in FIG. 20B.

The capturing room Ra contains the radiation irradiator 52. With reference to FIG. 1, the radiation irradiator 52 for capturing a long image is of a wide-angle radiation type that can simultaneously expose the multiple radiographic image capturing devices P1 to P3 loaded in the capturing stand 51A through a single exposure (one-shot exposure) of the patient H as the subject with radiation.

The capturing room Ra is provided with a relay 54 for relaying the communication between individual units inside the capturing room Ra and individual units outside the capturing room Ra. The relay 54 includes an access point 53 for wireless transmission of image data D and other signals from and to the radiographic image capturing devices P1 to P3. In FIGS. 1 and 2, the radiographic image capturing devices P1 to P3, which are loaded in the holder 51a of the capturing stand 51A, as described above, can be connected to the relay 54 via cables to establish communication. The relays 54 are connected to a controller 55 of the radiation irradiator 52 and the console C.

A console 57 of the radiation irradiator 52 is installed in a front chamber (operating chamber) Rb, as illustrated in FIG. 1. The console 57 includes an exposure switch 56 to be operated by an operator or radiologist to instruct the start of radiation to the radiation irradiator 52.

The front chamber Rb is provided with the console C composed of a computer (not shown) including a central processing unit (CPU), a read only memory (ROM), a random access memory (RAM), and an input/output interface, connected to each other via a bus. The radiographic image capturing system 50 having the configuration illustrated in FIG. 2 may include a console C disposed outside the capturing room.

The console C includes a display unit Ca including a cathode ray tube (CRT) or a liquid crystal display (LCD), and an input unit including a mouse and a keyboard (not shown). The console C is connected to an external or internal storage unit Cb including a hard disk drive (HDD). Although not illustrated, the console C is connected to a hospital information system (HIS), a radiology information system (RIS), and/or a picture archiving and communication system (PACS) via a network N.

In this embodiment, the console C functions as an image processor. Hereinafter, the console C functioning as an image processor will be referred to as image processor C. Alternatively, the image processor and the console C may be provided in the form of separate units.

[Radiographic Image Capturing Devices]

Figure 3:
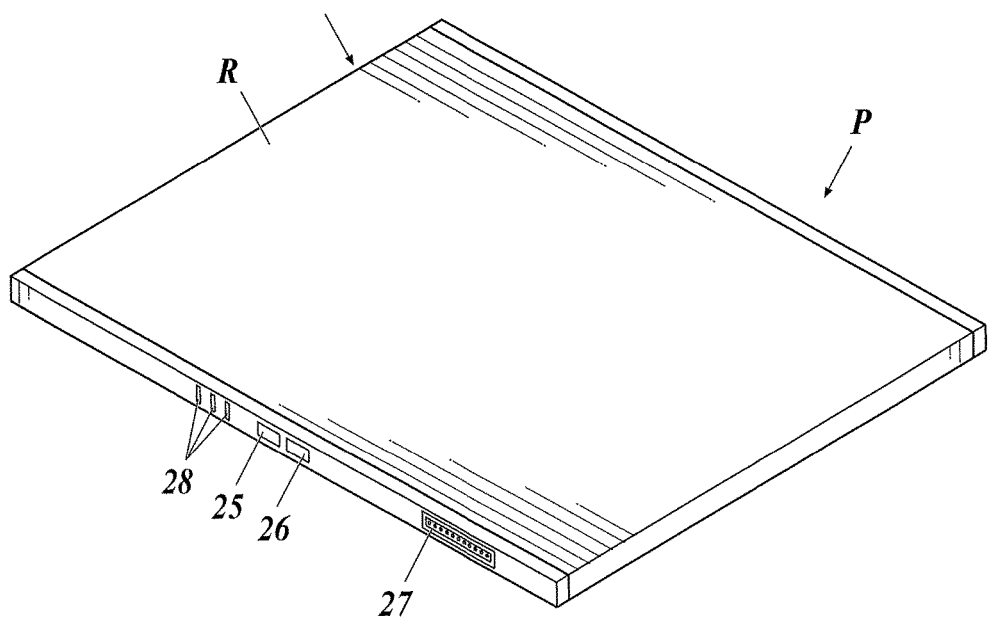
FIG. 3 is a perspective view illustrating the exterior of a radiographic image capturing device.

The radiographic image capturing devices P used in the radiographic image capturing system will now be described. FIG. 3 is a perspective view illustrating the exterior of a radiographic image capturing device.

The radiographic image capturing devices P according to this embodiment each includes a casing 2 accommodating radiation detectors 7 and other components described below. One of the side faces of the casing 2 is provided with a power switch 25, a selector switch 26, the connector 27 mentioned above, and indicators 28. Although not illustrated, for example, the opposite side face of the casing 2 according to this embodiment is provided with an antenna 29 (see FIG. 4) for wireless communication with external units. A cable (not shown) can be connected to the connector 27 to establish wire communication with an external unit.

Figure 4:
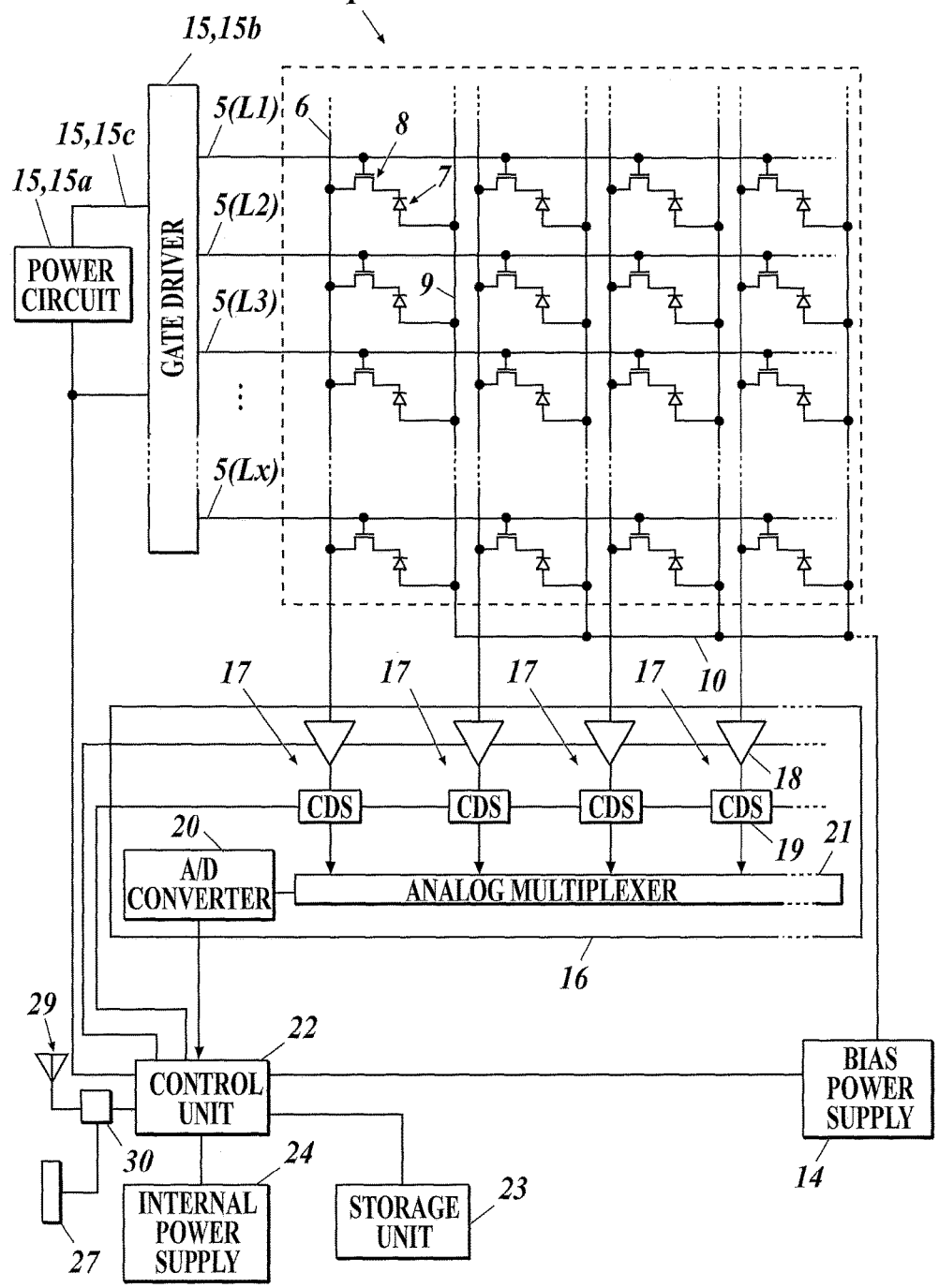
FIG. 4 is a block diagram illustrating the equivalent circuit of a radiographic image capturing device.

FIG. 4 is a block diagram illustrating the equivalent circuit of a radiographic image capturing device. With reference to FIG. 4, multiple radiation detectors 7 are disposed in a two-dimensional array or matrix on a sensor substrate (not shown) of a radiographic image capturing device P. The radiation detectors 7 each generate an electrical charge depending on the intensity of radiation. The radiation detectors 7 are connected to respective bias lines 9, which are connected to respective connecting lines 10. The connecting lines 10 are connected to a bias power supply 14. The bias power supply 14 applies an inverse bias voltage to the radiation detectors 7 via the bias lines 9.

The radiation detectors 7 are connected to thin film transistors (TFTs) 8, which serve as switching devices and are connected to respective signal lines 6. In a scan driver 15, a power circuit 15a supplies ON and OFF voltages to a gate driver 15b via a line 15c. The gate driver 15b switches the ON and OFF voltages applied to lines L1 to Lx of scanning lines 5. The TFTs 8 are turned on in response to an ON voltage applied via the scanning lines 5 and cause the electrical charge accumulated in the radiation detectors 7 to be discharged via the signal lines 6. The TFTs 8 are turned off in response to an OFF voltage applied via the scanning lines 5 to disconnect the radiation detectors 7 and the respective signal lines 6 and cause accumulation of the electrical charges in the radiation detectors 7.

Multiple reader circuits 17 are provided in a reader IC 16 and connected to the respective signal lines 6. During the reading process of image data D, electrical charges discharged from the radiation detectors 7 flow into the reader circuits 17 via the signal lines 6, and voltage values corresponding to the electrical charges are output from amplifier circuits 18. Correlated double sampling circuits ("CDSs" in FIG. 4) 19 read the voltage values from the amplifier circuits 18 and output analog image data items D corresponding to the voltage values to the components downstream. The image data items D are sequentially sent to an A/D converter 20 via an analog multiplexer 21, converted to digital image data items D at the A/D converter 20, and then stored in a storage unit 23.

A control unit 22 includes a computer (not shown) provided with a CPU, a ROM, a RAM, and an input/output interface connected to a bus, and a field programmable gate array (FPGA). The control unit 22 may be composed of a dedicated controller circuit. The control unit 22 is connected to the storage unit 23 provided with a static RAM (SRAM), a synchronous DRAM (SDRAM), and a NAND flash memory.

The control unit 22 is connected to a communication unit 30 that establishes wired or wireless communication with external units via an antenna 29 or a connector 27. The control unit 22 is further connected to an internal power supply 24, such as a lithium ion capacitor, that supplies electrical power to the functional units including the scan driver 15, the reader circuits 17, the storage unit 23, and the bias power supply 14.

Figure 5:
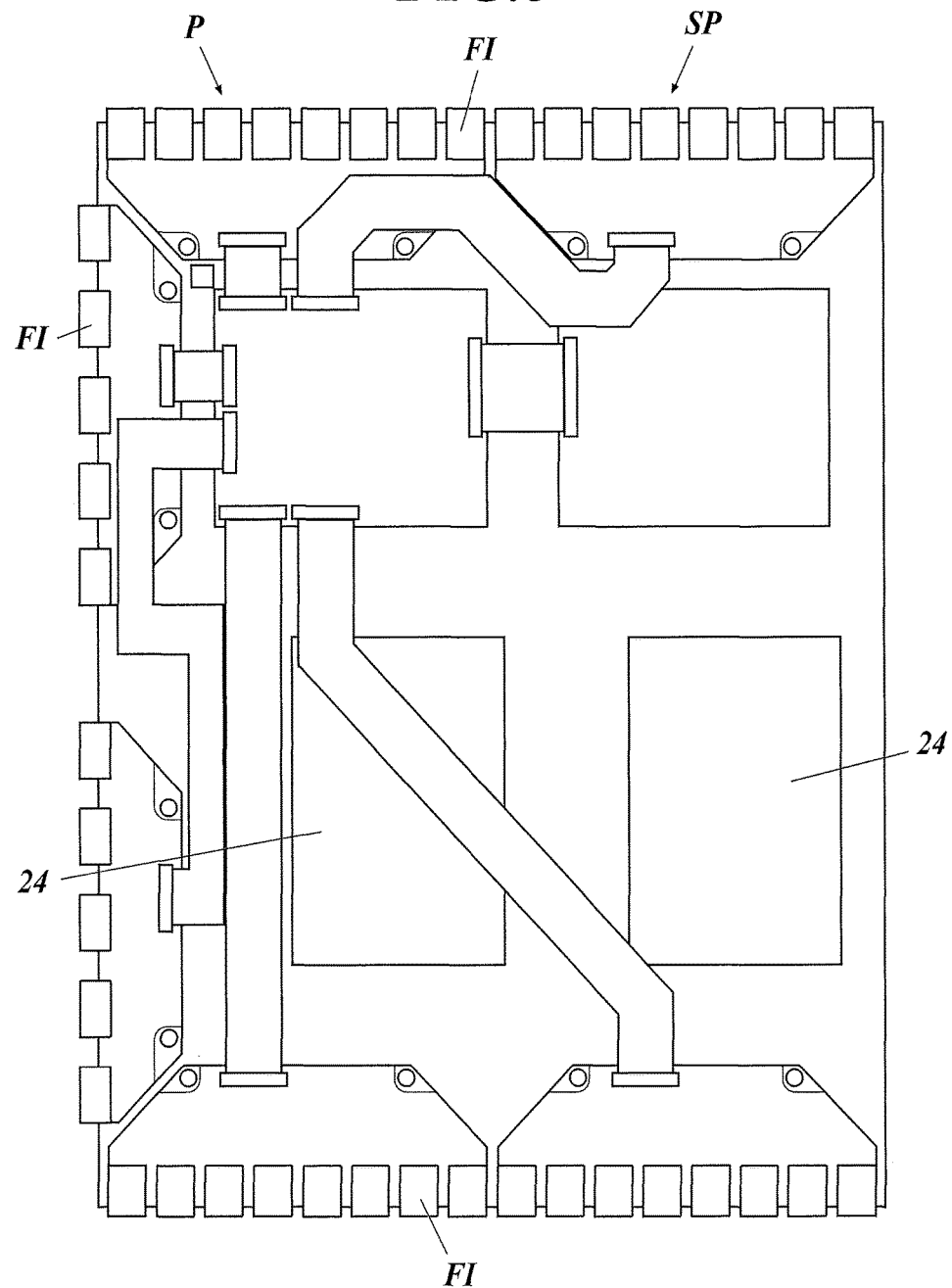
FIG. 5 illustrates an example configuration of a sensor panel of a radiographic image capturing device.

In this embodiment, each radiographic image capturing device P includes a sensor panel SP composed of a sensor substrate provided with multiple radiation detectors 7 and accommodated in a casing 2 (see FIG. 3). FIG. 5 illustrates an example configuration of the sensor panel and a rear view of the sensor panel SP (the face opposite from the radiation detectors 7). The front face of the sensor panel SP (provided with the radiation detectors 7) and the rear face (provided with the control unit 22) are connected via flexible circuit boards FI. The flexible circuit boards FI are each provided with a reader IC 16 (see FIG. 4) and gate ICs (not shown) constituting a gate driver 15b.

[Processes Carried Out at Radiographic Image Capturing System During Capturing of Long Image by One-Shot Exposure]

The processes carried out at the console C and the radiographic image capturing devices P1 to P3 loaded in the holder 51a of the capturing stand 51A during image capturing (i.e., the processes carried out before and after emission of radiation from the radiation irradiator 52 and the processes involving reading of image data D) are basically the same as known processes carried out in simple radiography, and thus, descriptions thereon are omitted.

Figure 22A:
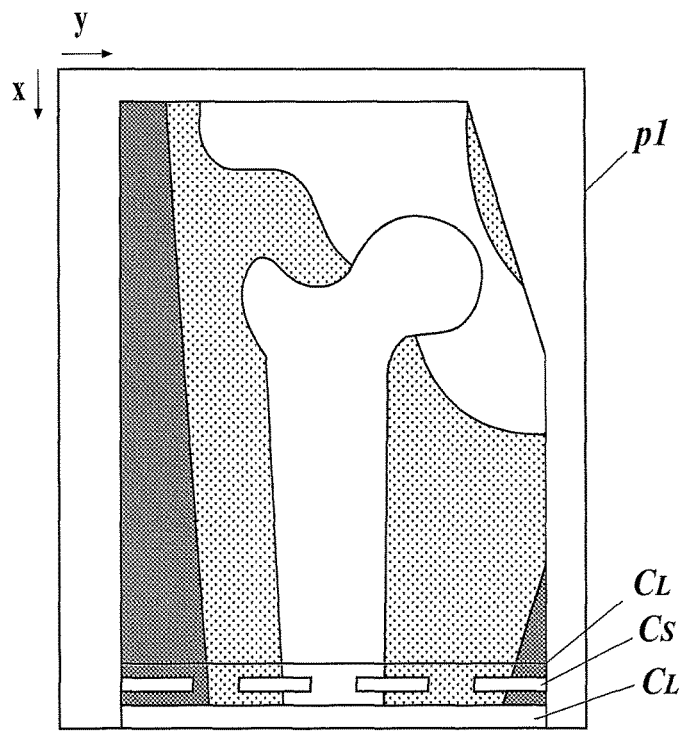
FIG. 22A illustrates streaky components and structural components in an image acquired by the rear radiographic image capturing device caused by the front radiographic image capturing device projected on the image.
Figure 22B:
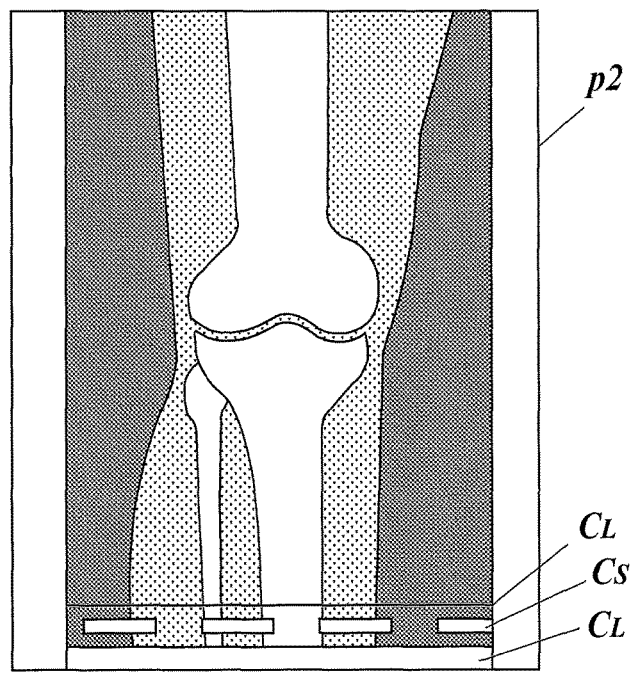
FIG. 22B illustrates streaky components and structural components in an image acquired by the rear radiographic image capturing device caused by the front radiographic image capturing device projected on the image.

Upon reception of image data sets D from the radiographic image capturing devices P1 to P3 and an offset data set O corresponding to an offset due to dark charges (also referred to as dark current) generated in the radiation detectors 7, the console C calculates the true image data set D* by subtracting the offset data set O from the image data set D for each radiation detector 7 in each radiographic image capturing devices P1 to P3 by expression (1), carries out precise image processing, such as gain correction, defective pixel correction, and gradation processing corresponding to the captured site, on the calculated true image data D*, to generate images p1 to p3 for the respective radiographic image capturing devices P1 to P3 (see FIGS. 22A and 22B).

$$D^* = D - O \tag{1}$$

Hereinafter, an image p generated on the basis of the image data D acquired by a radiographic image capturing device P, as described above, is referred to as an image p acquired by a radiographic image capturing device P. As illustrated in FIGS. 22A and 22B, the image p acquired by the rear radiographic image capturing device P among the images p1 to p3 acquired as described above by the respective radiographic image capturing devices P1 to P3 in the holder 51a contains transverse streaky components CL caused by linear structures, such as the edges of the casing 2 and the internal structure of the front radiographic image capturing device P and structural components CS caused by structures in the casing of the front radiographic image capturing device P.

Figure 6:
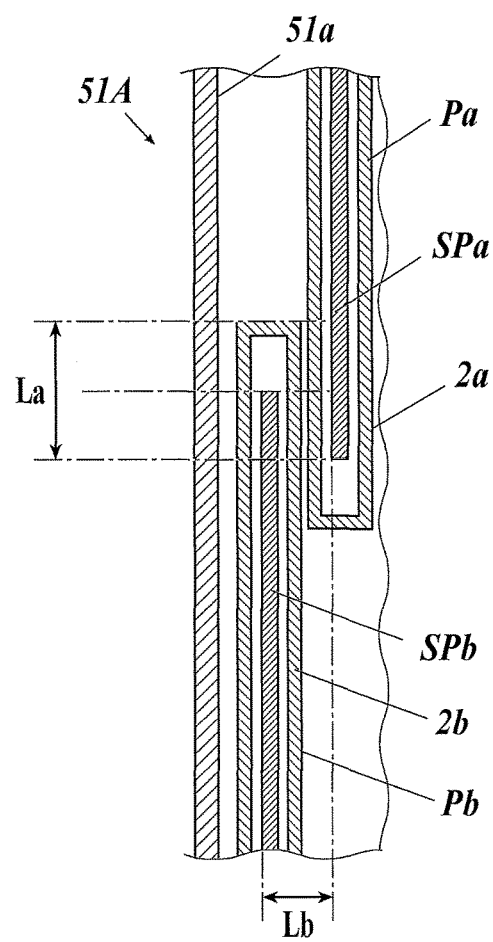
FIG. 6 illustrates a front radiographic image capturing device and a rear radiographic image capturing device in a holder of a capturing stand.

In the radiographic image capturing devices P loaded in the holder 51a of the capturing stand 51A according to this embodiment, as illustrated in FIG. 6, the upper edge of the bottom front radiographic image capturing device Pb overlaps in the anteroposterior direction with the lower edge of the top rear radiographic image capturing device Pa, for example.

The lower area of the image p acquired by the top rear radiographic image capturing device Pa contains streaky components CL caused by the linear edges at the top of the casing 2b and the top of the sensor panel SPb of the front radiographic image capturing device Pb and structural components CS caused by structures inside the casing, such as the reader IC 16 and the gate IC mounted on the flexible circuit board FI (see FIG. 5) mounted on the sensor panel SPb of the front radiographic image capturing device Pb. The reference signs La and Lb in FIG. 6 will be described below.

[Image Correction Process According to Present Invention]

An image correction process will now be described for the removal of the structural components CS and the streaky components CL from images p acquired by the radiographic image capturing devices P loaded in the holder 51a of the capturing stand 51A of the radiographic image capturing system 50 according to this embodiment. The operation of the radiographic image capturing system 50 according to this embodiment will also be described.

As described above, the structural components CS and the streaky components CL are caused by the casing 2 and the internal structures of the front radiographic image capturing device P projected on the image p acquired by the rear radiographic image capturing device P in the holder 51a of the capturing stand 51A. At the capturing stands illustrated in FIGS. 1, 20A, and 21, the image p1 acquired by the radiographic image capturing device P1 contains projections of the casing 2 and other structures of the radiographic image capturing device P2, and the image p2 acquired by the radiographic image capturing device P2 contains projections of the casing 2 and other structures of the radiographic image capturing device P3. The image p3 acquired by the radiographic image capturing device P3 at least does not contain projections of the casings 2 and other structures of the other radiographic image capturing devices P.

At the capturing stand illustrated in FIG. 20B, the image p2 acquired by the radiographic image capturing device P2 contains projections of the casings 2 and other structures of the radiographic image capturing devices P1 and P3, but the images p1 and p3 acquired by the radiographic image capturing devices P1 and P3, respectively, at least do not contain projections of the casings 2 and other structures of the other radiographic image capturing devices P.

What image p is to contain projections of the casings 2 and other structures of other radiographic image capturing devices P depends on the layout of the radiographic image capturing devices P in the holder 51a of the capturing stand 51A. In the description below, the rear radiographic image capturing device P is referred to as the radiographic image capturing device Pa, with reference to those exemplified in FIG. 6, and the image p acquired by the radiographic image capturing device Pa contains projections of the casing 2 and other structures of the front radiographic image capturing device Pb.

[Image Correction Process]

Figure 7:
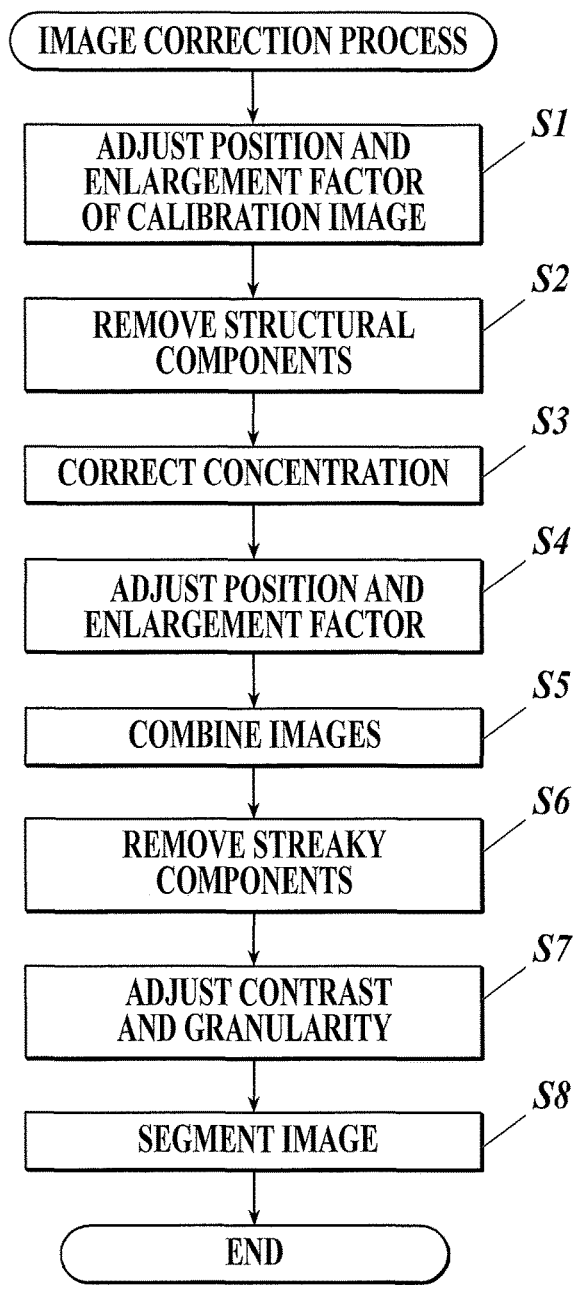
FIG. 7 is a flow chart illustrating the image correction process according to an embodiment.

The image correction process according to this embodiment is carried out in accordance with the flow chart illustrated in FIG. 7. In the example flow illustrated in FIG. 7, the image correction process includes removing the structural components CS from the image p and then removing the streaky components CL remaining in the image p. Alternatively, the streaky components CL may be removed from the image p and then the structural components CS remaining in the image p may be removed. The steps in the image correction process carried out in accordance with the flow chart illustrated in FIG. 7 will now be described.

[Preliminary Acquisition of Calibration Image]

Figure 8:
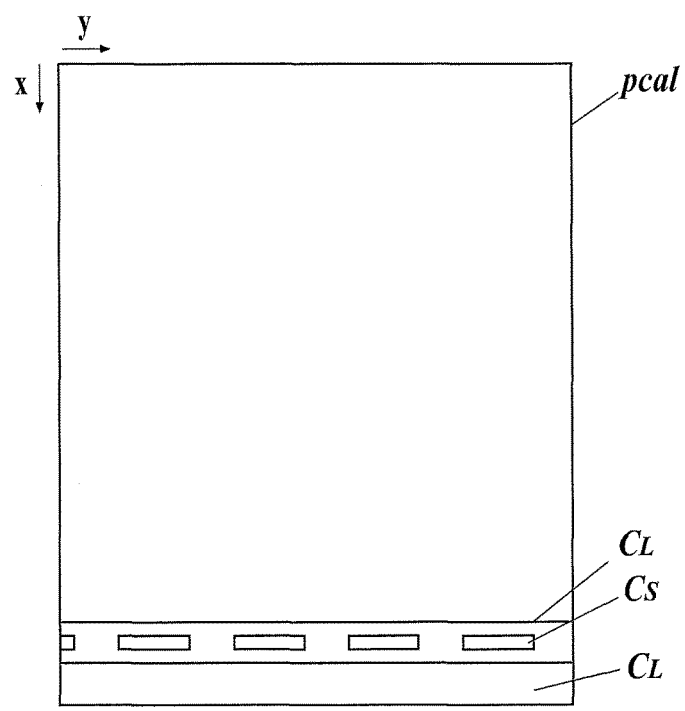
FIG. 8 illustrates an example calibration image.

A calibration image "pcal" processed in Step S1 in the flow chart in FIG. 7 will now be described. In this embodiment, a calibration image "pcal", such as that illustrated in FIG. 8, is generated through a process similar to that for the generation of an image p, as described above. That is, at least two radiographic image capturing devices Pa and Pb are loaded in adjacent loading positions in the holder 51a of the capturing stand 51A (i.e., the radiographic image capturing devices Pa and Pb are loaded in accordance with the layout illustrated in FIG. 6), radiation is emitted from the radiation irradiator 52 without the subject, and the calibration image "pcal" is generated based on the image data D acquired at the rear radiographic image capturing device Pa.

The calibration image "pcal" is a preliminarily captured image of the structural components CS and the streaky components CL caused by the radiographic image capturing device P loaded at the front position in the holder 51a of the capturing stand 51A and projected on the image p acquired by the rear radiographic image capturing device P. Calibration images "pcal" are preliminarily generated for every radiographic image capturing device P loadable in the holder 51a of the capturing stand 51A.

For example, calibration images "pcal" for a radiographic image capturing device P are acquired before shipment of the device P and/or after installation of the device P to a medical facility, such as a hospital. Alternatively, calibration images "pcal" may be acquired periodically or before every image capturing process. Identification information or a cassette ID of the radiographic image capturing device P is written in the header of data on the calibration image "pcal" to preliminarily establish a correspondence between the radiographic image capturing device P and the calibration image "pcal", and this correspondence is preliminarily stored in a database stored in a storage unit Cb of the image processor C (see FIGS. 1 and 2) or a storage unit in a server (not shown).

In this embodiment, the image processor C removes the structural components CS caused by the front radiographic image capturing device Pb from the image p acquired by the rear radiographic image capturing device Pa through capturing of a subject by one-shot exposure. In this removal process, the image processor C removes the structural components CS caused by the front radiographic image capturing device Pb projected on the image p on the basis of the calibration image "pcal" of the front radiographic image capturing device Pb and the image p acquired by the rear radiographic image capturing device Pa.

In this embodiment, the calibration image "pcal" is used in the step of removing the structural components in the image correction process.

[Loading Positions of Radiographic Image Capturing Device]

The radiographic image capturing device P that captures the calibration image "pcal" used for the removal of structural components is identified by the image processor C through determination of which one of the radiographic image capturing devices P is loaded in front of the rear radiographic image capturing device Pa during capturing of the image p.

For example, an operator or radiologist can instruct the image processor C to input cassette IDs of the radiographic image capturing devices P loaded at respective loading positions Q1 to Q3 (see FIG. 9A described below) in the holder 51a of the capturing stand 51A.

Although not shown, barcodes or tags, such as two-dimensional codes or radio frequency identification (RFID) tags, that include information such as the cassette IDs may be provided on the radiographic image capturing devices P, and readers may be provided at the loading positions Q1 to Q3 in the holder 51a of the capturing stand 51A. The codes or tags on the radiographic image capturing devices P loaded to the holder 51a by the operator or radiologist can be automatically read with the readers, and the identification information read by the readers (i.e., information on the loading positions) and the corresponding cassette IDs of the radiographic image capturing devices P loaded at the respective loading positions can be sent to the image processor C.

Figure 9A:
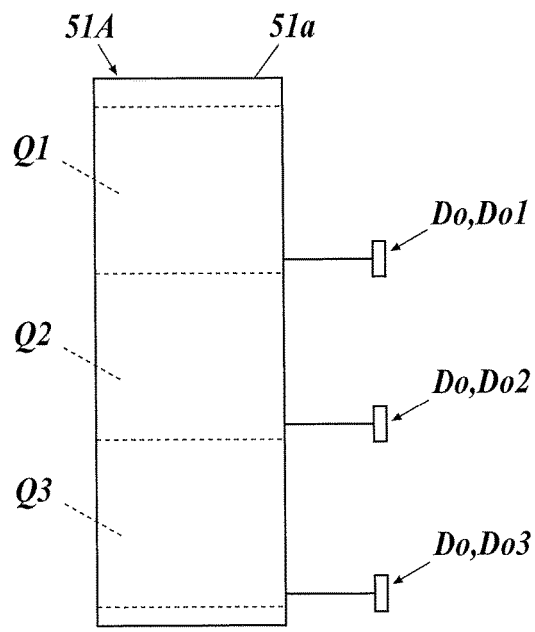
FIG. 9A illustrates loading positions and dongles disposed on a holder of the capturing stand.
Figure 9B:
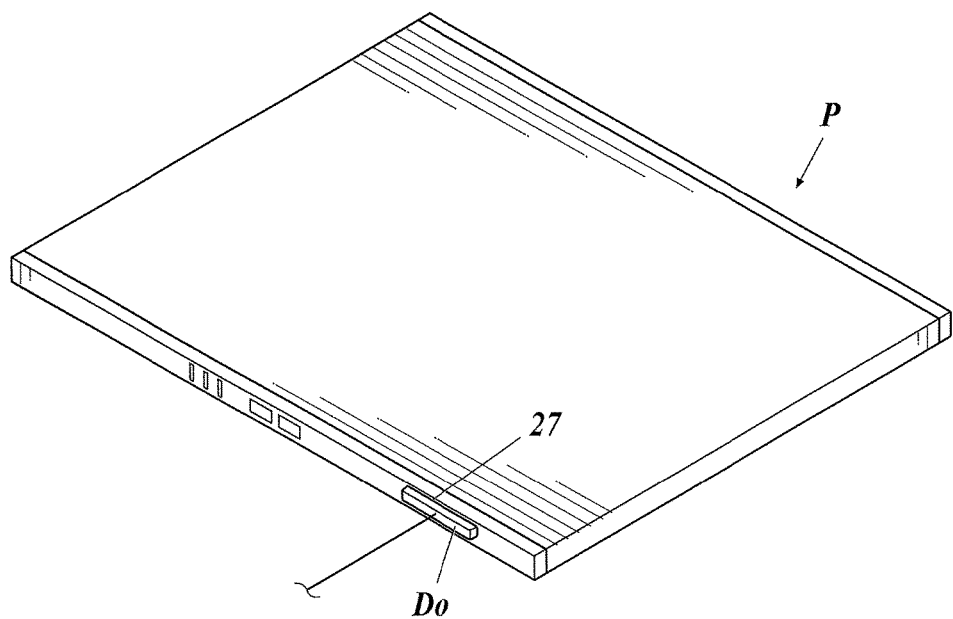
FIG. 9B illustrates a dongle in connection with a connector of a radiographic image capturing device.

With reference to FIG. 9A, dongles Do1 to Do3 that store respective identification information items are disposed at loading positions Q1 to Q3, respectively, in the holder 51a of the capturing stand 51A. With reference to FIG. 9B, the dongles Do are connected to connectors 27 provided on the respective radiographic image capturing devices P before the radiographic image capturing devices P are loaded to the holder 51a. Once a dongle Do is connected to a radiographic image capturing device P, the radiographic image capturing device P may read the identification information on the dongle Do (i.e., information on the loading positions) stored in the same dongle Do and send this information together with the cassette ID of the radiographic image capturing device P to the image processor C.

[Calculation of Position and Enlargement Factor of Calibration Image—Step S1]

The image processor C determines the image p to be corrected, i.e., the image p acquired by the rear radiographic image capturing device Pa, on the basis of the configuration of the holder 51a of the capturing stand 51A (i.e., the configuration illustrated in FIG. 1 or 20B) and the information on the loading positions Q1 to Q3 of the respective radiographic image capturing devices P1 to P3. Image correction is carried out on all of the images p acquired by the rear radiographic image capturing device Pa (for example, the two images p acquired by the respective radiographic image capturing devices P1 and P2 in FIG. 1, or the image p acquired by the radiographic image capturing device P2 in FIG. 20B).

The image processor C identifies the radiographic image capturing device Pb loaded in front of the rear radiographic image capturing device Pa, which captured the image p from which the structural components are to be removed, on the basis of the configuration of the holder 51a of the capturing stand 51A and the information on the loading positions Q of the radiographic image capturing devices P, and acquires the calibration image "pcal" for the identified radiographic image capturing device Pb.

The positional relationship between the front radiographic image capturing device Pb and the rear radiographic image capturing device Pa (i.e., the distance La between the lower edge of the sensor panel Spa of the rear radiographic image capturing device Pa (corresponding to the lower edge of the image p) and the upper edge of the casing 2b of the front radiographic image capturing device Pb and the distance Lb between the sensor panels Spa and SPb of the respective radiographic image capturing devices Pa and Pb, as illustrated in FIG. 6) during capturing of the calibration image "pcal" does not necessarily coincide with the positional relationship between the rear radiographic image capturing device Pa and the front radiographic image capturing device Pb during the actual capturing of a long image by one-shot exposure.

Although not shown, the distance SIDcal between the radiation irradiator 52 and the radiographic image capturing device Pa (Pb) during capturing of the calibration image "pcal" also does not always coincide with the distance SIDreal between the radiation irradiator 52 and the radiographic image capturing device Pa (Pb) during the actual capturing of a long image by one-shot exposure (see FIG. 1).

The image processor C adjusts the position of the image p and the position of the calibration image "pcal" to match each other on the basis of the information on the distances La and Lb during capturing of the calibration image written in the header of the calibration image "pcal" and the distances La and Lb during actual capturing of a long image by one-shot exposure. The adjustment of the positions can be carried out not only in the vertical direction (distance La) and the anteroposterior direction (distance Lb) but also in the transverse direction orthogonal to these directions.

Figure 10:
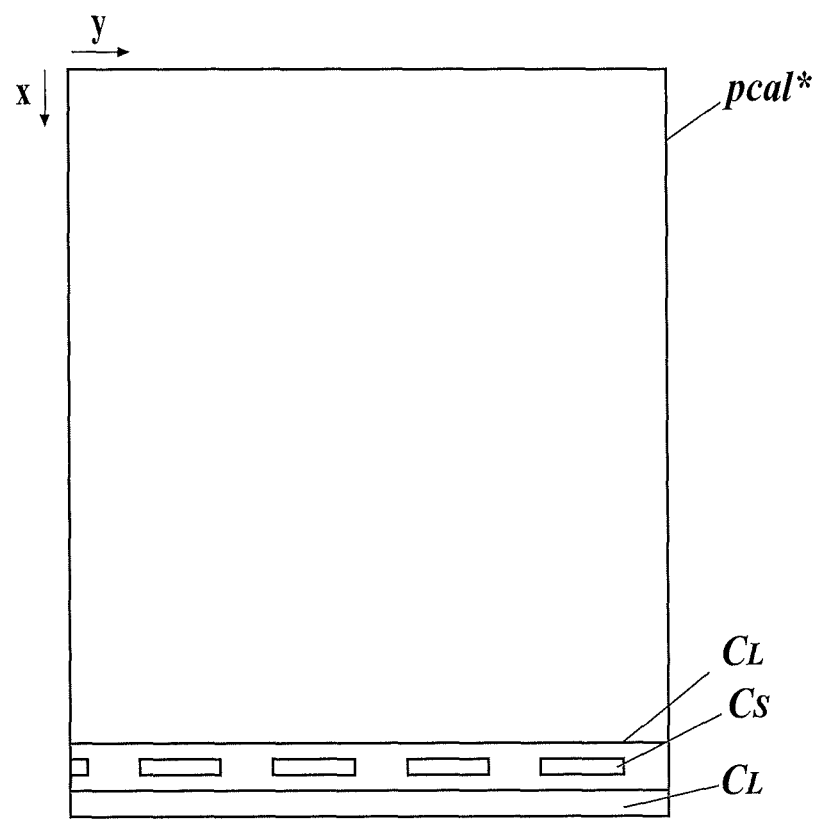
FIG. 10 illustrates an example calibration image after adjustment of positioning and enlargement factor.

The image processor C adjusts the enlargement factor of the calibration image "pcal" to match the enlargement factor of the image p on the basis of the distance SIDcal during capturing of the calibration image and the distance SIDreal during capturing of a long image by one-shot exposure, to generate an adjusted calibration image "pcal*", as illustrated in FIG. 10.

[Removal of Structural Components—Step S2]

The image processor C removes the structural components from the image p. In the removal of the structural components, the image processor C corrects the image p by appropriately increasing the pixel values f of the image p that are reduced due to the projection of structures, such as ICs, of the front radiographic image capturing device Pb (corresponding to an area in the image p containing the structural components CS) through application of the base image "ppanel", to remove the structural components CS from the image p.

Specifically, the image processor C generates a corrected image p by the following expression (2):

$$g(x,y)=f(x,y)+A(x,y)\times k(x,y) \quad (2)$$

where f(x,y) is a pixel value of a pixel (x,y) in the image p, k(x,y) is a pixel value of a pixel in the base image "ppanel", A(x,y) is a coefficient, and g(x,y) is a pixel value of a pixel in the corrected image p.

The image processor C generates a corrected image p by preparing abase image "ppanel" as described below. Specifically, the average value "have" is calculated as described above for the pixel values h(x,y) of the pixels in the area without streaky components CL and structural components CS in the adjusted calibration image "pcal*" (i.e., the top area in the image "pcal*" illustrated in FIG. 10), and the pixel values k(x,y) of the pixels in the base image "ppanel" are calculated by expression (3) for each pixel (x,y) in the adjusted calibration image "pcal*" containing the streaky components CL and the structural components CS:

$$k(x,y)=have-h(x,y) \quad (3)$$

where h(x,y) is a pixel value of a pixel (x,y) in the adjusted calibration image "pcal*" (see FIG. 10).

Figure 11A:
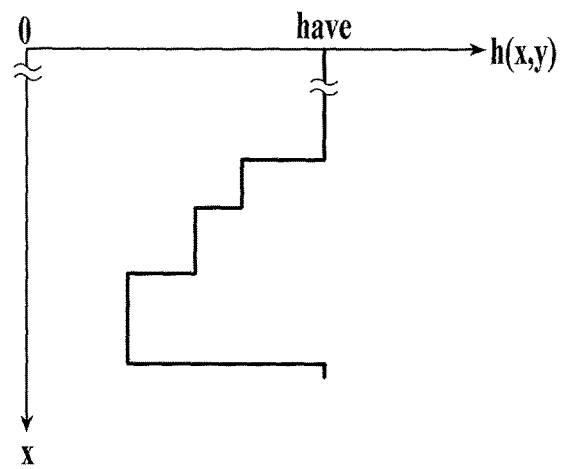
FIG. 11A is a graph illustrating a profile of pixel values of a pixel column in an adjusted calibration image.
Figure 11B:
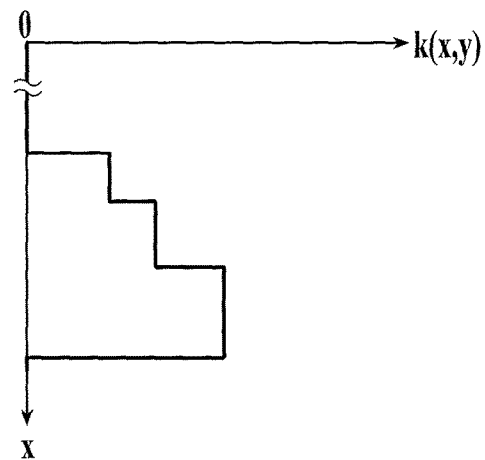
FIG. 11B is a graph illustrating a profile of pixel values of a pixel column in a base image.

Regarding the pixel values h (x,y) and k(x,y) in a pixel column in the adjusted calibration image "pcal*" (for example, a pixel column having a width of one pixel extending in the vertical direction as illustrated in FIG. 10) and a pixel column in the base image "ppanel", the pixel values h(x,y) of the adjusted calibration image "pcal*" substantially equal the average value "have" in areas without streaky components CL and structural components CS but are smaller than the average value "have" in the areas containing the streaky components CL and the structural components CS, as illustrated in FIG. 11A, whereas the pixel values h(x,y) of the base image "ppanel" are substantially zero in areas without streaky components CL and structural components CS but are positive values in the areas containing the streaky components CL and the structural components CS, as illustrated in FIG. 11B.

The inventors have conducted a research and discovered that a mere increase in the pixel values through addition of the pixel values k(x,y) of the pixels in the base image "ppanel", which are calculated as described above, and the pixel values f(x,y) of the pixels in the image p, as calculated by expression (4), cannot completely remove the edge components in the structural components CS (i.e., the boundary between the structural components CS and other areas) and results in visibly noticeable edge components remaining in the corrected image p.

$$g(x,y)=f(x,y)+k(x,y) \qquad (4)$$

In this embodiment, the pixel values k(x,y) of the pixels in the base image "ppanel" to be added to the pixel values f(x,y) of the pixels in the image p are multiplied by the coefficient A(x,y), which varies depending on the intensity of the edge components of the structural components CS (i.e., the variation in the pixel values at the boundary between the structural components CS and other areas), before addition to the pixel values f(x,y) of the pixels in the image p, as defined by expression (2), to precisely remove the structural components CS from the corrected image p.

Figure 12:
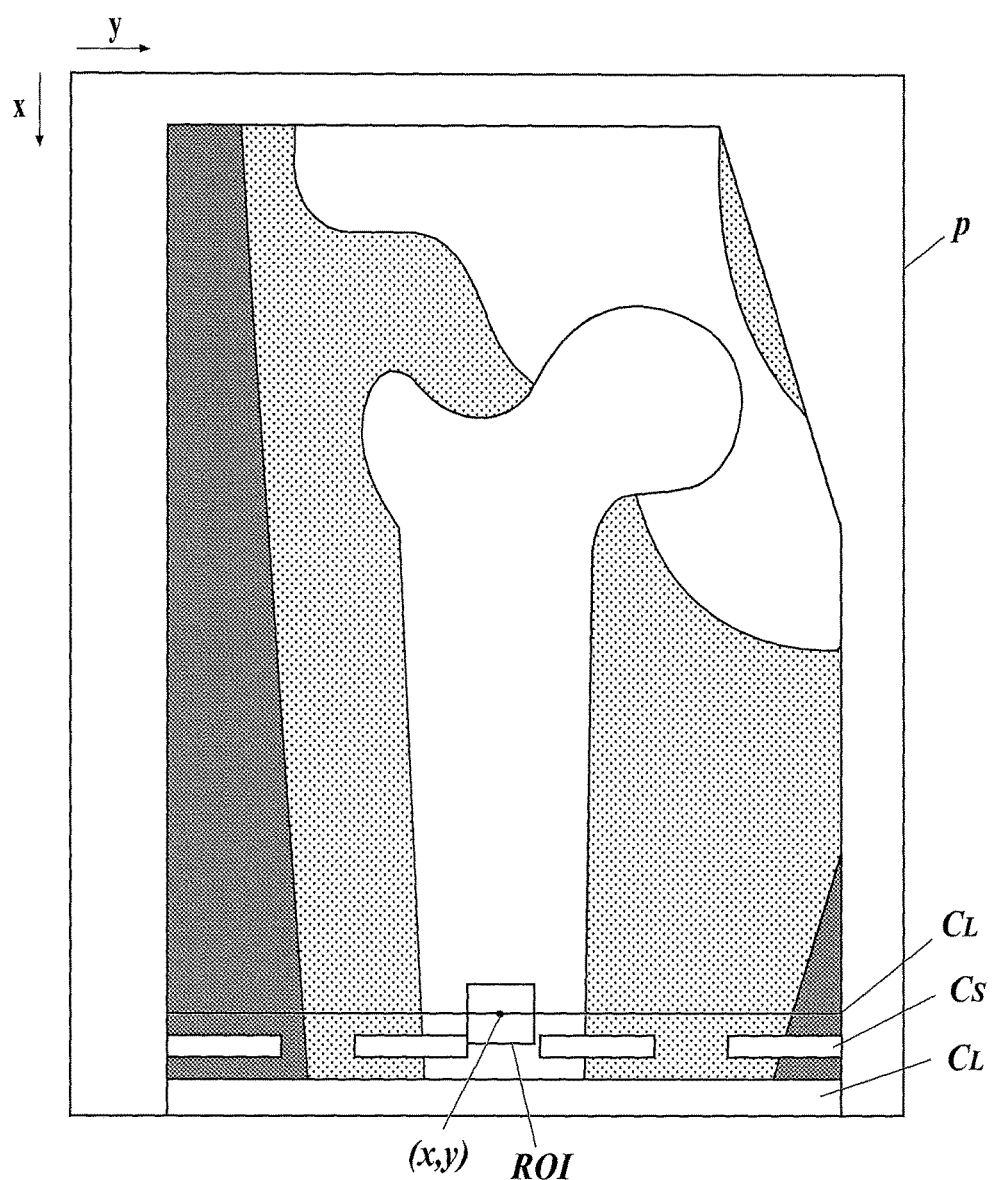
FIG. 12 illustrates an example region of interest assigned to an area centered on a target pixel in an image.

The image processor C calculates the coefficient A(x,y) by assigning a region of interest (ROI) of 100 by 100 pixels centered on one of the pixels (x,y) (i.e., a target pixel (x,y)) in the image p, as illustrated in FIG. 12, for example. The image processor C calculates evaluation functions e(x,y) for the pixels (x,y) in the ROI by expression (5), and defines the coefficient A(x,y) as the minimum sum of the evaluation functions e(x,y) of the pixels (x,y) in the ROI.

$$e(x,y)=\{g(x+1,y)-g(x-1,y)\}2+\{g(x,y+1)-g(x,y-1)\}2 \qquad (5)$$

The image processor C shifts the ROI in the image p and calculates the coefficients A(x,y) for the pixels (x,y) in the image p. The actual correction of the pixel values f(x,y) of the pixels in the image p by the expression (2) is only required in areas containing structural components CS and streaky components CL. Thus, the coefficients A(x,y) should only be calculated for such areas.

The area containing the structural components CS and the streaky components CL can be predetermined in the calibration image "pcal" to determine the area in which the position and enlargement factor in the calibration image "pcal" are adjusted as described above, i.e., the area in the image p containing the structural components CS and the streaky components CL. In this embodiment, the area in the image p containing the structural components CS and the streaky components CL are determined, and an ROI is assigned to the pixels in the areas.

That is, in this embodiment, the image processor C removes the structural components by calculating the values k(x,y) (i.e., the base image "ppanel") to be added to the pixel values f(x,y) of the pixels (x,y) in areas in the image p containing the structural components CS (see FIG. 12) based on the calibration image "pcal*" (see FIG. 10). The image processor C removes the structural components by calculating the corrected pixel values g(x,y) by adding the product of the coefficients A(x,y) and the corresponding values k(x,y) to the pixel values f(x,y), as defined by expression (2).

For the determination of a coefficient A(x,y), an ROI containing a target pixel (x,y) is assigned in the image p, as illustrated in FIG. 12. The coefficient A(x,y) is then defined as the minimum sum of the values e(x,y) (i.e., the intensity of the edge component) calculated by expression (5) (i.e., the evaluation factors) in the ROI.

In this embodiment, the image processor C removes the structural components as described above. Such a configuration allows appropriate correction of the image p and precise removal of the structural components CS from the image p.

At this point, complete removal of the streaky components CL is not accomplished, and some streaky components CL remain in the corrected image p. Thus, in this embodiment, the image processor C removes the streaky components CL remaining in the corrected image p in a subsequent step (Step S6 in FIG. 7).

[Correction of Concentration—Steps S3 to S5]

Figure 13A:
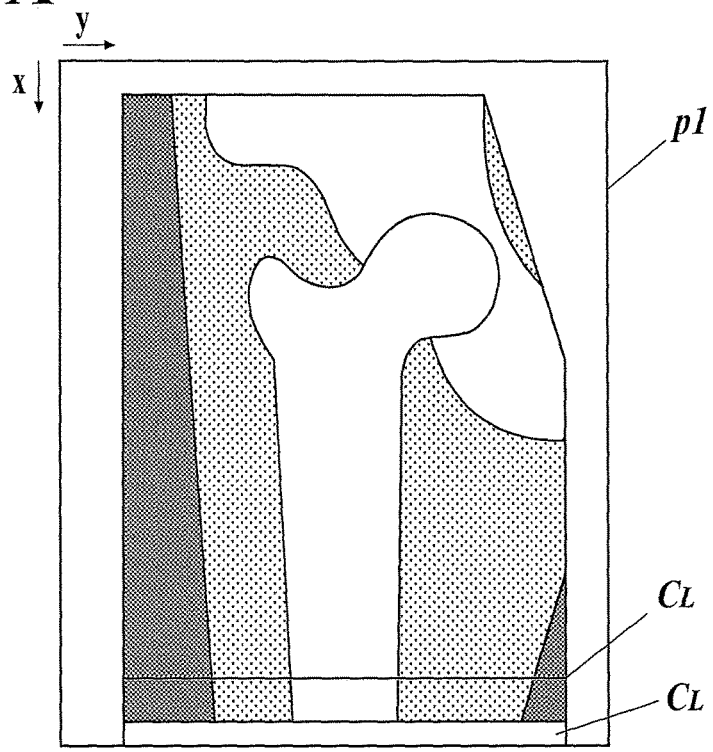
FIG. 13A illustrates a corrected image p1 from which structural components are removed.
Figure 13B:
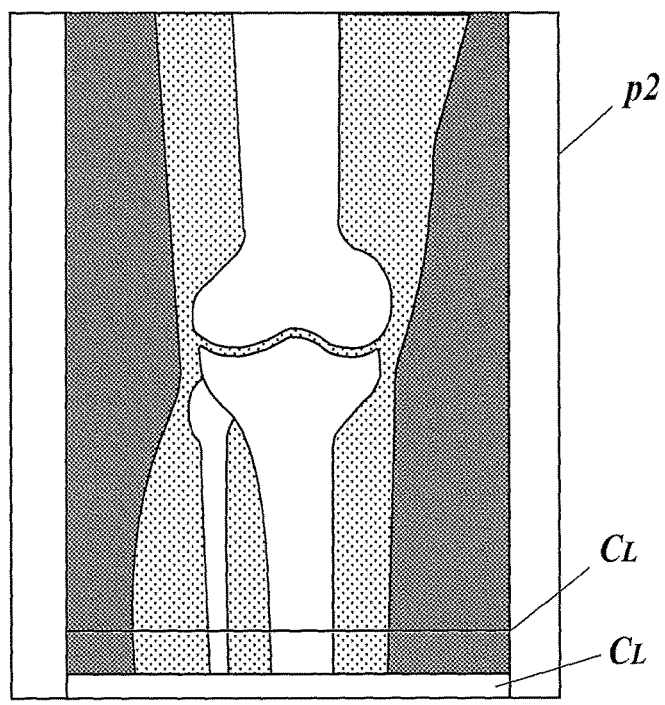
FIG. 13B illustrates a corrected image p2 from which structural components are removed.

In this embodiment, the image processor C removes the remaining streaky components CL from the image p corrected as described above by temporarily combining the corrected images p1 and p2 from which the structural components Cs are removed as described above, the images p1 and p2 being respectively acquired by radiographic image capturing devices P1 and P2 vertically adjacent in the holder 51a of the capturing stand 51A, as illustrated in FIGS. 13A and 13B.

Specifically, the image processor C corrects the concentration of the images p1 and/or p2 such that the concentration of the images p1 and p2 match each other (Step S3 in FIG. 7), adjusts the positional relationship and the enlargement factors of the images p1 and p2 (Step S4), and overlays the identical regions of the subject in the images p1 and p2, to smoothly connect the images p1 and p2 (Step S5).

Known schemes may be applied to the correction of concentration, the adjustment of positions and enlargement factors, and combination of the images (Steps S3 to S5). Details of such schemes are disclosed in Japanese Patent Application Laid-Open Nos. 2002-44413, 2002-85392, and 2002-94772, for example. The techniques described in these specifications are processes of combining images captured by computed radiography (CR) cassettes. These techniques can also be effectively applied to processes of combining the images p captured by the radiographic image capturing devices P.

In a case where a radiographic image capturing device P3 is loaded at a loading position Q3 in the holder 51a of the capturing stand 51A, the radiographic image capturing devices P1 and P2 are not projected on the image p3 captured by the radiographic image capturing device P3. Thus, the image p3 should not require removal of structural components. After the concentration is corrected (Step S3) and the positions and enlargement factor are adjusted (Step S4), the images p1, p2, and p3 are combined.

In a typical process of generating a long image "plong" through combination of two images, the connecting area of the two images (overlapping area) contains only the image captured by the radiographic image capturing device Pb, which is loaded at the front position in the holder 51a of the capturing stand 51A (for example, the image captured by the front radiographic image capturing device Pb in FIG. 6), and does not contain the image captured by the rear radiographic image capturing device Pa, which is loaded at the rear position in the holder 51a of the capturing stand 51A, because the front radiographic image capturing device Pb may be projected on the connecting area (overlapping area) in the image captured by the rear radiographic image capturing device Pa.

In this embodiment, the images p1 and p2 are temporarily combined to remove the streaky components. Thus, in the step of combining the images (Step S5), the connecting area (overlapping area) of the images p1 and p2 to be combined contain the remaining streaky components CL captured by the radiographic image capturing devices P loaded in the rear positions in the holder 51a of the capturing stand 51A (i.e., the radiographic image capturing devices P1 and P2 respective to the radiographic image capturing devices P2 and P3), unlike the images used in the process described above.

Figure 14:
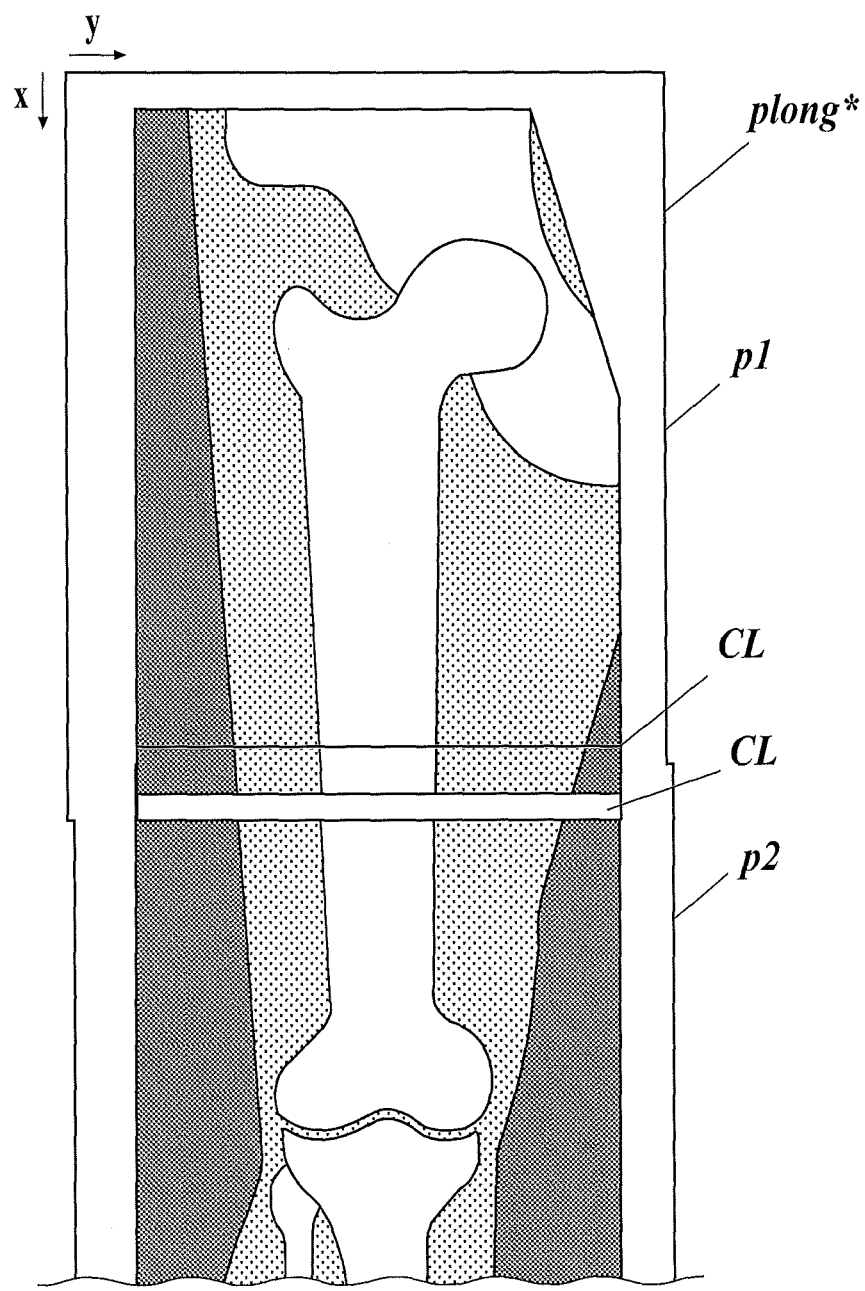
FIG. 14 illustrates an example combined image generated through combination of images p1 and p2 illustrated in FIGS. 13A and 13B, respectively.

In this embodiment, the combined image "plong*" contains a streaky component CL remaining in the image p1 in the connecting area (overlapping area) of the two images (for example, images p1 and p2), as illustrated in FIG. 14. Although not shown, the connecting area of the images p2 and p3 (overlapping area) also contains streaky components CL that remained in the image p2.

Hereinafter, an image acquired through combination of images p, as described above, is referred to as combined image "plong*" for differentiation from a long image "plong" combined through a typical scheme.

[Removal of Streaky Components—Step S6]

The image processor C removes the streaky components CL residing or remaining in the combined image "plong*" on the basis of the combined image "plong*" generated as described above (Step S6 in FIG. 7). The removal of the streaky components CL from the connecting area of the images p1 and p2 of the combined image "plong*" (see FIG. 14) will now be described. The streaky components CL in the connecting area of the images p2 and p3 are also removed in a similar process.

Figure 15:
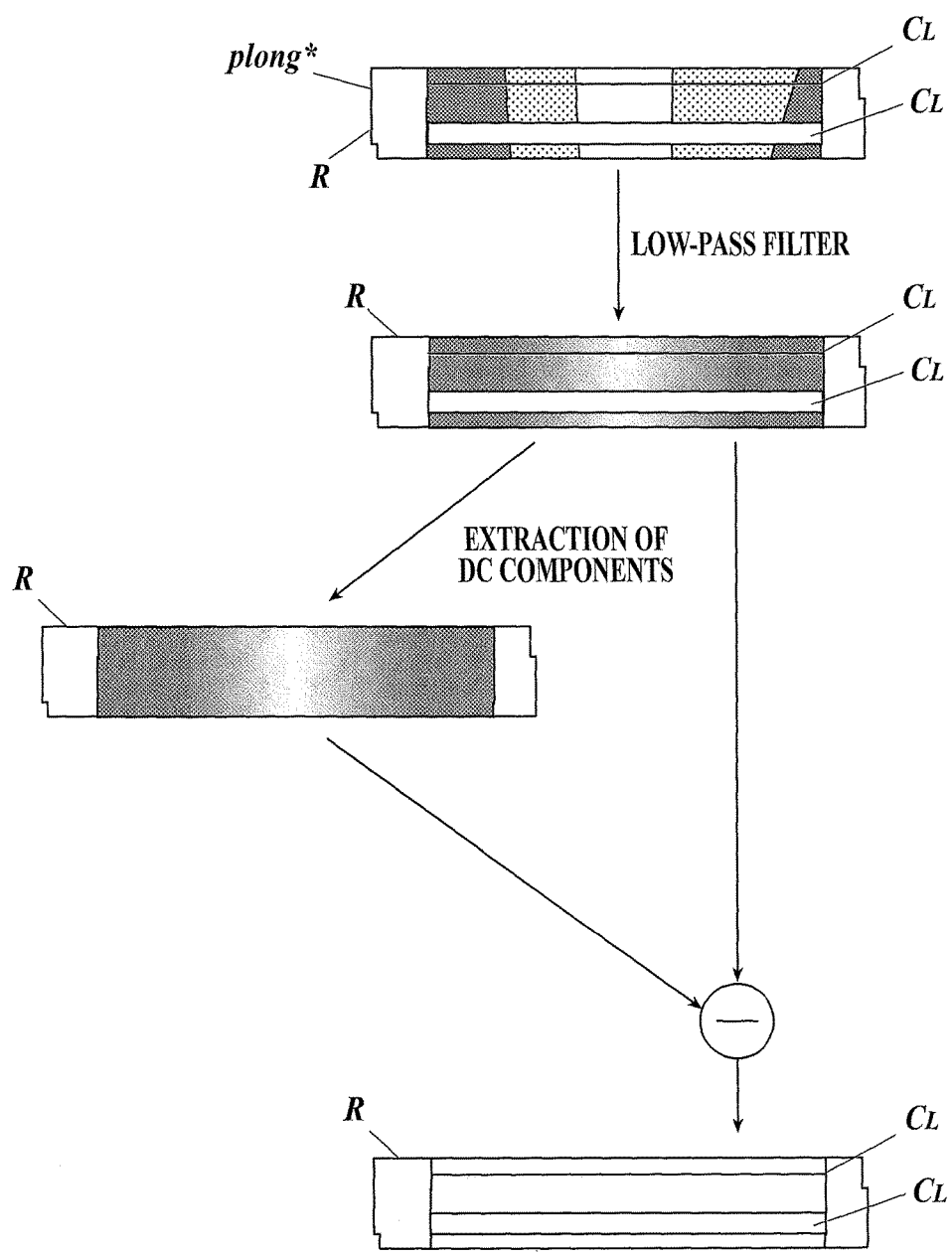
FIG. 15 illustrates an example scheme for extraction of streaky components in a region R in a combined image.

In this embodiment, the streaky components are removed as follows. The streaky components CL can be regarded as horizontal low-frequency components (along the y direction in FIG. 14) in the combined image "plong*". With reference to FIG. 15, the image processor C extracts a region R containing the streaky components CL in the combined image "plong*", applies a low-pass filter, such as a Gaussian filter, in the horizontal direction of the region R (i.e., a pixel row having a width of one pixel extending in the horizontal direction), and smooths the streaky components CL along the horizontal direction.

As described above, the area containing the streaky components CL in the combined image "plong*", i.e., the area containing the streaky components CL in the image p1, can be determined on the basis of the area containing the streaky components CL in the calibration image "pcal". Thus, the region R in the combined image "plong*" containing the streaky components CL can be assigned to a region equivalent to the area containing the streaky components CL plus a predetermined number of pixels added to the top and bottom edges, for example.

Smoothing of the streaky components CL through the low-pass filter can be controlled and varied on the basis of information on the subject and edges in the pixel rows to be smoothed.

The region R of the combined image "plong*" passing through the low-pass filter along the horizontal direction contains the smoothed streaky components CL superimposed on background DC components. Thus, the image processor C extracts the DC component from the region R of the combined image "plong*" after passing the combined image "plong*" through the low-pass filter.

Specifically, with reference to FIG. 16, the image processor C selects pixel rows Lp1 and Lp2, each having a width of one pixel, from areas above and below a region Rc containing the streaky components CL, in other words a region Rc other than the region containing the streaky components CL, within the region R containing the streaky components CL, in the combined image "plong*" passing through the low-pass filter.

The image processor C performs linear interpolation by expression (6), for example, on pixel values g(x,y) upper of pixels in the upper pixel row Lp1 and corresponding pixel values g(x,y) lower of pixels in the lower pixel row Lp2 (i.e., pixels on different pixel columns at the same y coordinates), to calculate the pixel values g*(x,y) of the pixels between the pixel rows Lp1 and Lp2.

$$g^*(x,y) = t \times g(x,y)\text{upper} + (1-t) \times g(x,y)\text{lower} \quad (6)$$

where $0 \leq t \leq 1$.

The image processor C carries out such calculation on the pixel columns (every y coordinate) in the region R of the combined image "plong*" passing through the low-pass filter, to extract the DC component from the region R (see FIG. 15). In the region R including areas above and below the pixel rows Lp1 and Lp2, respectively, as illustrated in FIG. 16, the DC components of these areas are defined as the pixel values g(x,y) of the pixels in these areas.

If the image processor C selects pixel rows Lp1 and Lp2 of pixels having significantly different pixel values g(x,y), the DC components acquired through linear interpolation will be significantly different from the actual DC components. Thus, it is preferred that the image processor C selects pixel rows Lp1 and Lp2 that have similar average pixel values g(x,y) of the pixels in the pixel rows Lp1 and Lp2, respectively.

With reference to FIG. 15, the image processor C subtracts the DC components extracted as described above from the region R of the combined image "plong*" passing through the low-pass filter, and removes the background of the region R of the combined image "plong*" passing through the low-pass filter, to extract the streaky components CL residing or remaining in the region R. That is, the DC components g*(x,y) of the pixels in the background (pixel values g(x,y) for pixels in the areas above and below the pixel rows Lp1 and Lp2, respectively) are subtracted from the pixel values g(x,y) of the pixels in the region R in the combined image "plong*" passing through the low-pass filter, to extract the streaky components CL.

The image processor C adds the extracted streaky components CL to the pixel values g(x,y) of the pixels corresponding to the combined image "plong*" (see FIG. 14), to remove the streaky components CL from the combined image "plong*".

In the removal of streaky components according to this embodiment (Step S6 in FIG. 7), the image processor C subtracts the DC components from the components acquired through the smoothing with a low-pass filter along the horizontal direction of the region R containing the streaky components CL and assigned in an image p or the combined image "plong*", to extract the streaky components CL (see FIG. 15), and adds the extracted streaky components CL to the pixel values g(x,y) of the pixels corresponding to the image p or the combined image "plong*", to remove the streaky components CL from the image p or combined image "plong*".

In this embodiment, the image processor C removes the streaky components as described above to suitably correct the combined image "plong*" or images p1 and p2, to precisely remove the streaky components CL residing or remaining in the combined image "plong*" or the images p1 and p2.

As a result of extracting the region R, which contains the streaky components CL, from an image p or the combined image "plong*", and adding the streaky components CL extracted from the region R through the processes illustrated in FIG. 15 to the pixel values g(x,y) of the pixels corresponding to the image p or the combined image "plong*" (see FIG. 14), as described above, the areas inside or outside the boundary of the region R in the image p or the combined image "plong*" and/or the pixel rows Lp1 and Lp2 selected as described above could include a fluctuation in pixel values.

In such a case, in the process of adding the streaky components CL extracted as described above to the image p or the combined image "plong*" from which the streaky components are removed, the products of the streaky components CL and a coefficient are added to the image p or combined image "plong*" so as to prevent the fluctuation (or significantly reduce it to a non-visible level) and smooth the areas of the image p and the combined image "plong*" above and below the fluctuation (i.e., smoothing).

[Adjustment of Contrast and Granularity—Step S7]

Even after image correction is carried out as described above to remove the structural components CS and the streaky components CL (Steps S3 and S6) from the combined image "plong*" or images p1 and p2 (hereinafter, collectively referred to as combined image "plong*"), the contrast and granularity of the areas in the combined image "plong*" from which the structural components CS and the streaky components CL are removed may have contrast and granularity different from those of other areas in the combined image "plong*".

After the image processor C removes the structural components CS and the streaky components CL from the combined image "plong*", as described above, the contrast and granularity of the overall combined image "plong*" can be adjusted to matched values (Step S7 in FIG. 7). That is, the contrast and granularity of the areas of the combined image "plong*" from which the structural components CS and the streaky components CL are removed are matched to the contrast and granularity of the other areas in the combined image "plong*" (in particular, the periphery of the removed structural components CS and streaky components CL). Such image processing can be performed to match the contrast and granularity of the different areas in the combined image "plong*", making the areas in the combined image "plong*" from which the structural components CS and the streaky components CL are removed indistinguishable from the other areas.

The contrast and granularity can be adjusted so that the horizontal lines above and below the seam of combined images have similar frequency components, for example. Specifically, (1) high-frequency components above the seam are blurred or smoothed; (2) an unsharp mask is applied below the seam to enhance the high-frequency components; and (3) the high-frequency components above and below the seam are measured and adjusted to match each other. The process returns to step (1) and repeated, as necessary. In step (3), a Fourier transform spectrum or other statistical indices may be used as a measurement index.

In another scheme, the amplification factors of the contrast and granularity can be preliminarily defined in each area that contains structural components CS and streaky components CL caused by the projection of the front radiographic image capturing device Pb in the image p captured by the rear radiographic image capturing device Pa; the areas in the image p from which the structural components CS and the streaky components CL are removed as described above are resolved into low, intermediate, and high frequency image components; and the product of the intermediate frequency image components and the amplification factor of contrast, the product of the high frequency image components and the amplification factor of granularity, and these products are added to the low frequency image components, to achieve uniform contrast and granularity.

The amplification factors of the contrast and granularity may be 1 or more or less than 1. An amplification factor of 1 or more enhances contrast and granularity, whereas an amplification factor of less than 1 smooths contrast and granularity. The high frequency information removed from the image after adjustment can be recovered through the use of a Wiener filter. Such a technique is effective in making an indistinguishable seam between images having different qualities.

[Generation of Long Image]

Figure 17:
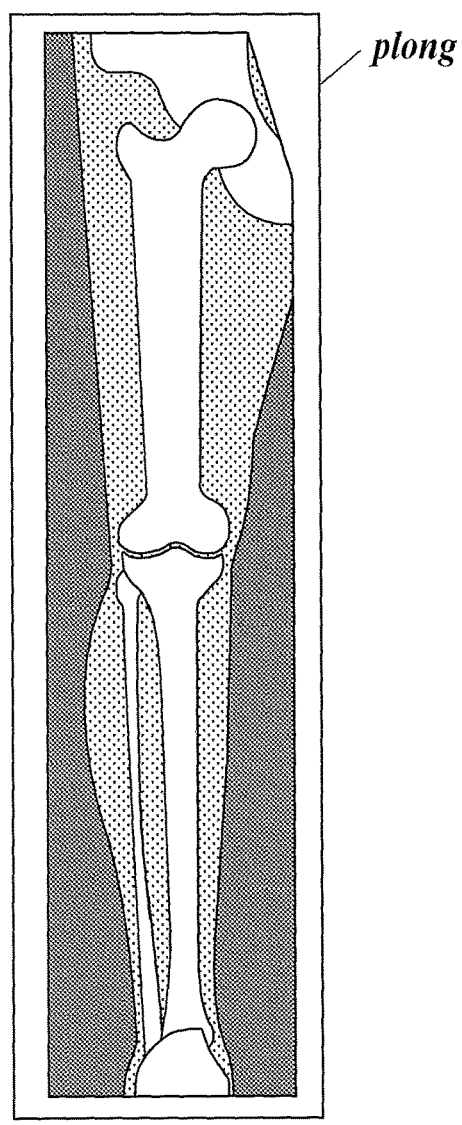
FIG. 17 illustrates an example long image.

As described above, the image processor C corrects the combined image "plong*" through removal of structural components and streaky components and adjusts the contrast and granularity, as required, to acquire a combined image "plong*" equivalent to a long image "plong", such as that illustrated in FIG. 17. Thus, the image processor C can generate a long image "plong" through image correction on the combined image "plong*", as described above.

As described above, in the generation of a typical long image "plong" through combination of images p1 and p2 (or images p1 to p3), the connecting area (overlapping area) of the images p contain an image captured by the radiographic image capturing device Pb loaded in the front position in the holder 51a of the capturing stand 51A (for example, the image captured by the front radiographic image capturing device Pb in FIG. 6). In contrast, in the connecting step (Step S5) in the image correction process according to this embodiment (see FIG. 7), the connecting area (overlapping area) of the images p contains an image p captured by the radiographic image capturing device Pa loaded in the rear position in the holder 51a of the capturing stand 51A.

Alternatively, in this embodiment, a long image "plong" can be generated in accordance with the process of generating a typical long image "plong".

[Segmentation—Step S8]

In this embodiment, the image processor C corrects the combined image "plong*" through removal of structural components and streaky components, as described above, adjusts the contrast and granularity, as required, and segments the processed combined image "plong*" into images p1 to p3 (Step S8 in FIG. 7). To differentiate the images p1 to p3 captured by the radiographic image capturing devices P1 to P3, respectively, loaded in the holder 51a of the capturing stand 51A, the images acquired through segmentation of the processed combined image "plong*" will hereinafter be referred to as images p*1 to p*3.

Figure 18A:
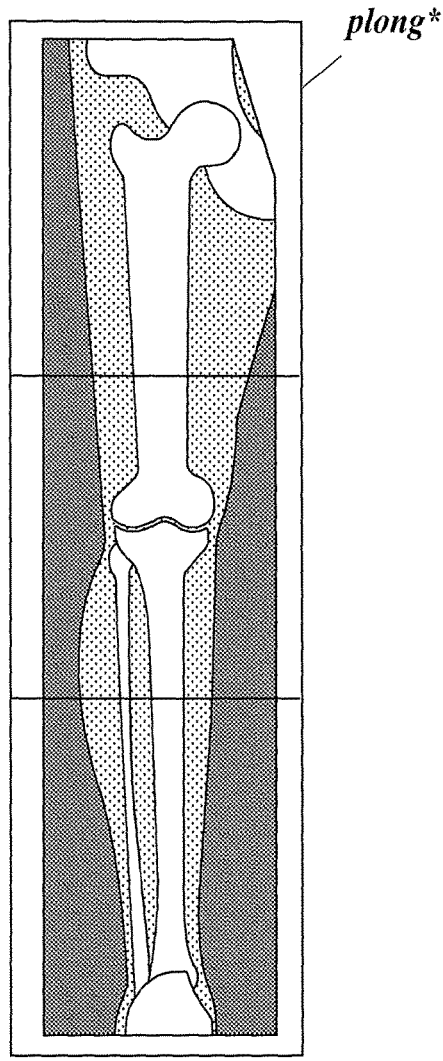
FIG. 18A illustrates the segmentation of a processed combined image.

In the segmentation (Step S8), the image processor C segments the processed combined image "plong*" at the bottom edges of the images p1 and p2, as illustrated in FIG. 18A, prior to combination (see FIGS. 13A and 13B) to generate images p*1 to p*3. Simple segmentation of the processed combined image "plong*" could cause loss in the image p*2 in the overlapping area of the images p1 and p2, which are combined after the concentration correction (Step S3 in FIG. 7) and the adjustment of the position and enlargement factor (Step S4). Similarly, a portion of the image p*3 could be lost in the overlapping area of the images p2 and p3 that are combined.

Among the images p*1 to p*3 generated through the segmentation of the processed combined image "plong*," a portion of the image p*2 corresponding to the overlapping area of the combined images p1 and p2 and a portion of the image p*3 corresponding to the overlapping area of the combined images p2 and p3 are respectively added to the top edges of the images p*2 and p*3, which are generated through segmentation.

Figure 18B:
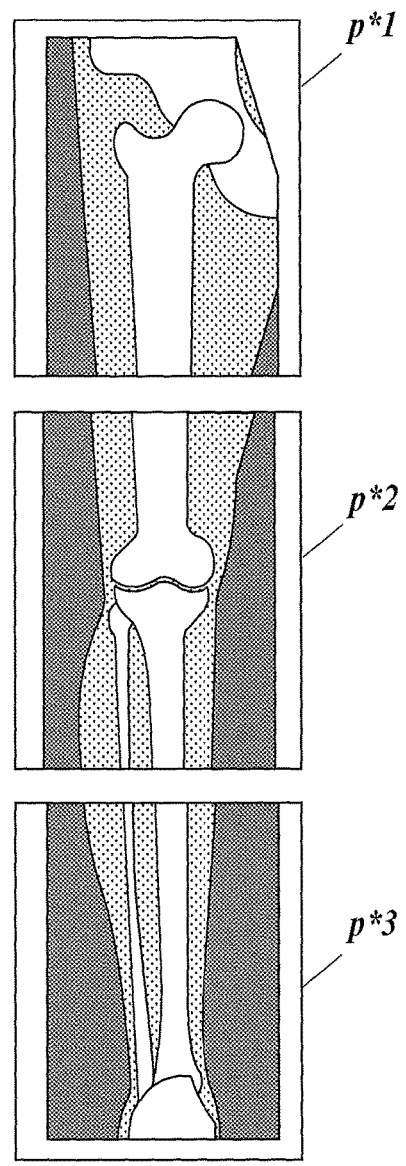
FIG. 18B illustrates example images from which structural components and streaky components are removed.

In this embodiment, the images p*1 and p*2 generated by the image processor C through segmentation of the combined image "plong*", as illustrated in FIG. 18B, are derived from the images p1 and p2 through removal of the structural components CS and the streaky components CL (and the adjustment of the contrast and granularity, as required).

In other words, the structural components CS and the streaky components CL can be precisely removed from the images p1 and p2 acquired by the rear radiographic image capturing devices P1 and P2, respectively, loaded in the holder 51a of the capturing stand 51A. Since the segmented image p*3 does not contain structural components CS and streaky components CL in the first place, the segmented image p*3 is identical to the original image p3.

Advantageous Effects

In the radiographic image capturing system 50 according to this embodiment as described above, the image processor C can remove the structural components CS and the streaky components CL (see FIGS. 12, 22A, and 22B) caused by the front radiographic image capturing device Pb projected on the image p acquired by the rear radiographic image capturing device Pa loaded in the holder 51a of the capturing stand 51A for capturing a long image by one-shot exposure (see FIG. 6).

By image correction on the image p, the images p acquired through capturing of a long image by one-shot exposure can be precisely corrected, and images p*1 to p*3 (see FIG. 18B) can be acquired through precise removal of the structural components CS and the streaky components CL from the corrected images p. The images p*1 to p*3 can be combined to precisely generate a long image "plong" (see FIG. 17).

In contrast to the embodiment described above, image correction can be carried out by removing the streaky components in the images p and then removing the structural components CS remaining in the images p, as described above.

Figure 19:
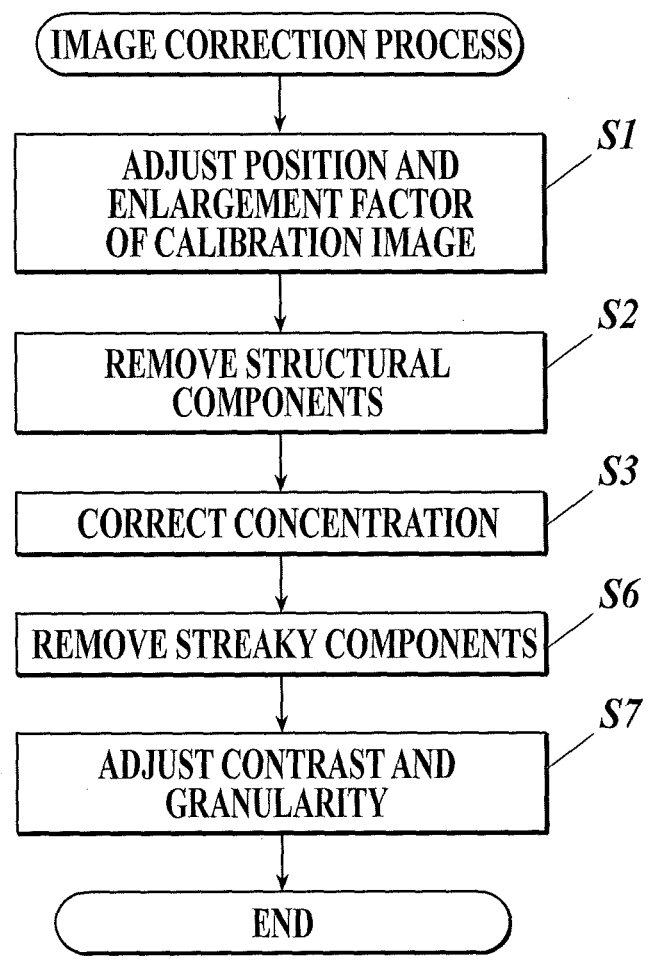
FIG. 19 is a flow chart illustrating another process of image correction.

In the embodiment described above, the images p1 to p3 acquired by the respective radiographic image capturing devices P1 to P3 loaded in the holder 51a of the capturing stand 51A during image capturing are temporarily combined by the image processor C, and streaky components are removed from the combined image "plong*" (Step S6 in FIG. 7). Alternatively, as illustrated in FIG. 19, for example, the streaky components can be removed from the images p1 and p2 without combination of the images p1 to p3.

In the embodiment described above, as illustrated in FIG. 16, the pixel row Lp1 having a width of one pixel is selected from the image p1, and the pixel row Lp2 having a width of one pixel is selected from the image p2. The pixel rows Lp1 and Lp2 are linearly interpolated by expression (6) to calculate the DC components, which are background components of the region R required for the removal of streaky components. Unfortunately, the removal of the streaky components from each of the images p1 and p2, as described, precludes the selection of at least the pixel row Lp2 having a width of one pixel.

In such a case, for example, the streaky components can be removed from each of the images p1 and p2 as in the embodiment described above using data on a pixel row having a width of one pixel at the top of the image p2 for the removal of the streaky components from the image p1 and using data on a pixel row having a width of one pixel at the top of the image p3 for the removal of the streaky components from the image p2.

Figure 16:
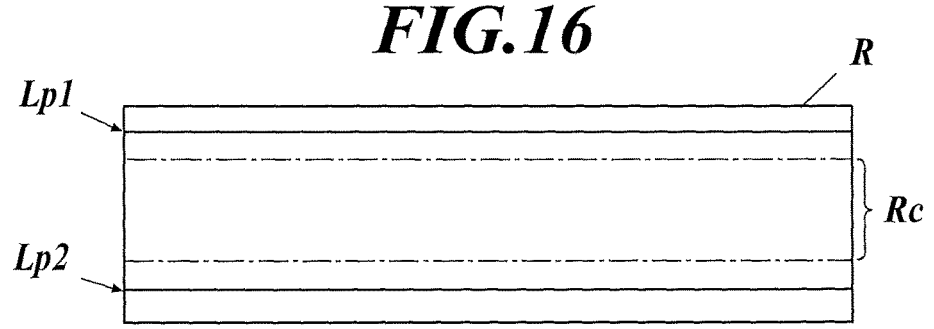
FIG. 16 illustrates pixel rows Lp1 and Lp2 selected from the region R.

For example, during removal of the streaky components from the image p1, pixel rows Lp1 and Lp2 both having a width of one pixel may be selected from the image p1 above a range Rc (see FIG. 16), and the pixel row Lp2 can be presumed to be present in the image p1 below the range Rc, as illustrated in FIG. 16. In this way, the streaky components can be removed from each of the images p1 and p2 as in the embodiment described above.

[Images without Projection of Structural Component]

Depending on the structure of the front radiographic image capturing device Pb (see FIG. 6) loaded in the holder 51a of the capturing stand 51A, the image p captured by the rear radiographic image capturing device Pa could contain the streaky components CL without the structural components CS or with structural components CS which are hardly visible.

In such a case, as in the embodiment described above, the images p1 to p3 can be combined to remove the streaky components, or the streaky components can be removed from each of the individual images p1 and p2 without combination of the images p1 to p3. In such a case, the Steps S1 and S2 in the flow chart illustrated in FIGS. 7 and 19, for example, are unnecessary, and thus the calibration image "pcal" is also unnecessary. The removal of the streaky components is then carried out as illustrated in FIG. 15.

In the removal of streaky components from a combined image "plong*" generated through the combination of the images p1 to p3 or from each of the individual images p1 and p2 without combination of the images p1 to p3, image processing is carried out as described above to match (enhance or smooth) the contrast and granularity in the areas of the combined image "plong*" or the images p1 and p2 from which the streaky components CL are removed to the other areas of the combined image "plong*" or the images p1 and p2 (in particular, the periphery of the removed structural components CS and streaky components CL).

Through such configuration, areas in the combined image "plong*" or the images p1 and p2 from which the structural components CS and the streaky components CL are removed can be indistinguishable from other areas, as described above.

The present invention is not limited to the above embodiments and modifications, and can be suitably changed without leaving the scope of the present invention.

This application is based upon and claims the benefit of priority from the Japanese Patent Application No. 2015-082439, filed Apr. 14, 2015, the entire contents of which are incorporated herein by reference.

What is claimed is:

1. A radiographic image capturing system comprising:
a capturing stand which includes a holder which is able to hold a plurality of radiographic image capturing devices;
a radiation irradiator which is able to irradiate the radiographic image capturing devices loaded in the holder at once with radiation; and
an image processor which generates a plurality of images based on image data acquired by the radiographic image capturing devices,
wherein,
an edge of a front radiographic image capturing device overlaps in an anteroposterior direction with an edge of a rear radiographic image capturing device in the holder in view from the radiation irradiator, the front radiographic image capturing device being a radiographic image capturing device close to the radiation irradiator among the radiographic image capturing devices loaded in the holder, the rear radiographic image capturing device being a radiographic image capturing device remote from the radiation irradiator among the radiographic image capturing devices loaded in the holder, the image processor removes a structural component derived from the front radiographic image capturing device projected on a generated image, on the basis of a calibration image and the generated image, the calibration image being preliminarily generated based on the image data acquired by the rear radiographic image capturing device irradiated with radiation with no subject disposed in front of the radiographic image capturing devices loaded in the holder of the capturing stand, the generated image being generated based on the image data acquired by the rear radiographic image capturing device during actual image capturing of a subject, and the image processor removes a streaky component residing in the generated image on the basis of the generated image, to correct the image.

2. The radiographic image capturing system according to claim 1, wherein, the image processor corrects the image through removal of the structural component and removal of the streaky component remaining in the image after the removal of the structural component.

3. The radiographic image capturing system according to claim 2, wherein, the image processor removes the structural component from each image generated based on the image data acquired by each radiographic image capturing device loaded in the holder of the capturing stand, combines the images from which the structural component is removed, and removes the streaky component remaining in a combined image generated by combining the images.

4. The radiographic image capturing system according to claim 3, wherein, the image processor combines the images at an overlapping area of the images, the overlapping area including the image captured by the rear radiographic image capturing device in the holder of the capturing stand.

5. The radiographic image capturing system according to claim 1, wherein, the image processor corrects the image through removal of the streaky component and removal of the structural component remaining in the image after the removal of the streaky component.

6. The radiographic image capturing system according to claim 1, wherein, during removal of the structural components, the image processor, calculates a value k(x,y) based on the calibration image, the value k(x,y) being added to a pixel value f(x,y) of a pixel (x,y) in an area of the image on which the structural component of the front radiographic image capturing device is projected, calculates a corrected pixel value g(x,y) determined by adding the product of the value k(x,y) and a coefficient A(x,y) to the pixel value f(x,y), as defined by an expression (1), to remove the structural component:

$$g(x,y)=f(x,y)+A(x,y)\times k(x,y) \quad (1), \text{ and}$$

determines the coefficient A(x,y) as a minimum sum of a value e(x,y) calculated by an expression (2) within a region of interest assigned to include a target pixel on the image:

$$e(x,y)=\{g(x+1,y)-g(x-1,y)\}^2+\{g(x,y+1)-g(x,y-1)\}^2 \quad (2)$$

7. The radiographic image capturing system according to claim 1, wherein, during removal of the streaky component, the image processor, subtracts a background component from a component acquired through horizontal smoothening of a region assigned in the image containing the streaky component, to extract the streaky component, and adds the extracted streaky component to a pixel value of each pixel in the image, to remove the streaky component from the image.

8. The radiographic image capturing system according to claim 1, wherein, the image processor corrects the image and carries out image processing to adjust contrast and granularity of an area of the image from which the structural component and the streaky component are removed to match the contrast and granularity with another area in the image.

9. The radiographic image capturing system according to claim 8, wherein, the process of adjusting the contrast and the granularity of the image includes resolving an area of the corrected image from which the structural component and the streaky component are removed into images having different frequency bands, multiplying the images having different frequency bands with a predetermined amplification factor, and adding together the images having different frequency bands multiplied with the amplification factor.

10. A radiographic image capturing system comprising:

a capturing stand which includes a holder which is able to hold a plurality of radiographic image capturing devices;

a radiation irradiator which is able to irradiate the radiographic image capturing devices loaded in the holder at once with radiation; and an image processor which generates a plurality of images based on image data acquired by the radiographic image capturing devices, wherein, an edge of a front radiographic image capturing device overlaps in an anteroposterior direction with an edge of a rear radiographic image capturing device in the holder in view from the radiation irradiator, the front radiographic image capturing device being a radiographic image capturing device close to the radiation irradiator among the radiographic image capturing devices loaded in the holder, the rear radiographic image capturing device being a radiographic image capturing device remote from the radiation irradiator among the radiographic image capturing devices loaded in the holder, the image processor removes a streaky component residing in the generated image based on the generated image, to correct the image, and the image processor subtracts a background component from a component acquired through horizontal smoothing of a region assigned in the image containing the streaky component during removal of the streaky component, to extract the streaky component, and adds the extracted streaky component to a pixel value of each pixel in the image, to remove the streaky component from the image.

11. The radiographic image capturing system according to claim 10, wherein, the image processor corrects the image and carries out image processing to adjust contrast and granularity of an area of the image from which the streaky component is removed to match the contrast and granularity with another area of the image.

12. The radiographic image capturing system according to claim 11, wherein, the process of adjusting the contrast and the granularity of the image includes resolving an area of the corrected image from which the streaky component is removed into images having different frequency bands, multiplying the images having different frequency bands with a predetermined amplification factor, and adding together the images having different frequency bands multiplied with the amplification factor.

13. An image processor for use with a plurality of radiographic image capturing devices and a radiation irradiator which is able to irradiate the radiographic image capturing devices loaded in the holder at once with radiation, wherein an edge of a front radiographic image capturing device overlaps in an anteroposterior direction with an edge of a rear radiographic image capturing device in the holder in view from the radiation irradiator, the front radiographic image capturing device being a radiographic image capturing device close to the radiation irradiator among the radiographic image capturing devices loaded in the holder, the rear radiographic image capturing device being a radiographic image capturing device remote from the radiation irradiator among the radiographic image capturing devices loaded in the holder the image processor comprising:

a processor configured to:

process a radiographic image captured by overlapping edges of the plurality of radiographic image capturing devices;

remove a structural component derived from the front radiographic image capturing device projected on a generated image, on the basis of a calibration image and the generated image, the calibration image being preliminarily generated based on the image data acquired by the rear radiographic image capturing device irradiated with radiation with no subject disposed in front of the radiographic image capturing devices loaded in the holder of the capturing stand, the generated image being generated based on the image data acquired by the rear radiographic image capturing device during actual image capturing of a subject.

* * * * *